United States Patent
Tang et al.

(10) Patent No.: US 9,737,616 B2
(45) Date of Patent: Aug. 22, 2017

(54) COMPOUNDS AND METHODS FOR THE TREATMENT OF ERB B2/NEU POSITIVE DISEASES

(71) Applicant: Bio-Thera Solutions, Ltd., Co., Guangzhou (CN)

(72) Inventors: Weijia Tang, Guangzhou (CN); Shengfeng Li, Belmont, CA (US); Jin-Chen Yu, Palo Alto, CA (US); Xiaobin Deng, Guangzhou (CN)

(73) Assignee: Bio-Thera Solutions, Ltd., Co., Science (CN)

( * ) Notice: Subject to any disclaimer, the term of this patent is extended or adjusted under 35 U.S.C. 154(b) by 0 days.

(21) Appl. No.: 14/802,900

(22) Filed: Jul. 17, 2015

(65) Prior Publication Data
US 2015/0320881 A1   Nov. 12, 2015

Related U.S. Application Data

(62) Division of application No. 13/837,187, filed on Mar. 15, 2013, now abandoned.

(30) Foreign Application Priority Data

Dec. 21, 2012 (CN) .......................... 2012 1 0563916
Mar. 14, 2013 (CN) .......................... 2013 1 0081880

(51) Int. Cl.
C07K 16/28      (2006.01)
A61K 47/48      (2006.01)
A61K 31/537     (2006.01)
C07K 16/32      (2006.01)

(52) U.S. Cl.
CPC ...... *A61K 47/48561* (2013.01); *A61K 31/537* (2013.01); *A61K 47/48384* (2013.01); *A61K 47/48407* (2013.01); *A61K 47/48584* (2013.01); *A61K 47/48715* (2013.01); *A61K 47/48723* (2013.01); *C07K 16/32* (2013.01)

(58) Field of Classification Search
None
See application file for complete search history.

(56) References Cited

U.S. PATENT DOCUMENTS

| | | |
|---|---|---|
| 3,896,111 A | 7/1975 | Kupchan et al. |
| 4,137,230 A | 1/1979 | Hashimoto et al. |
| 4,256,746 A | 3/1981 | Miyashita et al. |
| 4,260,608 A | 4/1981 | Miyashita et al. |
| 5,208,020 A | 5/1993 | Chari et al. |
| 5,416,064 A | 5/1995 | Chari et al. |
| 6,333,410 B1 | 12/2001 | Chari et al. |
| 7,598,375 B2 | 10/2009 | Ho et al. |
| 8,877,706 B2 | 11/2014 | Li et al. |
| 8,889,855 B2 | 11/2014 | Deng |
| 9,314,536 B2 | 4/2016 | Qin et al. |
| 9,345,786 B2 | 5/2016 | Li et al. |
| 2006/0167245 A1 | 7/2006 | Widdison et al. |
| 2010/0129314 A1 | 5/2010 | Singh et al. |
| 2012/0121615 A1 | 5/2012 | Flygare et al. |
| 2014/0178413 A1 | 6/2014 | Tang et al. |

FOREIGN PATENT DOCUMENTS

EP          0021173 A1    1/1981

OTHER PUBLICATIONS

Gerdes et al. (Front. Oncol. Dec. 18, 2014 doi: 10.3389/fonc.2014.00366, pp. 1-12).*
Kaiser (Science, 2006, 313: 1370).*
The National Cancer Institute (Lymphoma-Patient Version http://www.cancer.gov/types/lymphoma downloaded Dec. 17, 2015).*
Krontiris and Capizzi (Internal Medicine, 4th Edition, Editor-in-chief Jay Stein, Elsevier Science, 1994 Chapters 71-.*
Carter, S. K. et al. (Chemotherapy of Cancer; Second edition; John Wiley & Sons: New York, 1981; appendix C).*
Van Noort and Amor (International Rev. of Cytology, 1998, vol. 178, Cell Biology of Autoimmune Diseases, pp. 127-206).*
Feldmann and Steinman (Nature Jun. 2, 2005, 435: 612-619, IDS).*
Cassady, John M., et al., Recent Developments in the Maytansinoid Antitumor Agents, Chem. Pharm. Bull., Jan. 2004, pp. 1-26, vol. 52, No. 1, Pharmaceutical Society of Japan.
Desmyter, Aline, et al., Crystal structure of a camel single-domain VH antibody fragment in complex with lysozyme, Nature Structural Biology, Sep. 1996, pp. 803-811, vol. 3, No. 9, Nature Publishing Group, http://www.nature.com/nsmb.
Greenberg, A.S., et al., A new antigen receptor gene family that undergoes rearrangement and extensive somatic diversification in sharks, Nature, Mar. 9, 1995, pp. 168-73, vol. 374.
Greene, T.W., et al., Protecting Groups in Organic Synthesis, 1999, Third Edition, Wiley, New York.
Hudziak, R.M., et al.,p185HER2 Monoclonal Antibody Has Antiproliferative Effects In Vitro and Sensitizes Human Breast Tumor Cells to Tumor Necrosis Factor, Molecular and Cellular Biology, Mar. 1989, pp. 1165-1172, vol. 9, No. 3, American Society for Microbiology.
Ishiyama, Munetaka, et al., A Combined Assay of Cell Viability and in Vitro Cytotoxicity with a Highly Water-Soluble Tetrazolium Salt, Neutral Red and Crystal Violet, Biol. Pharm. Bull. 1996, vol. 19, No. 11, Pharmaceutical Society of Japan.
Issel, B., et al., Maytansine, 5 Cancer Treatment Reviews, 1978, pp. 199-207.
Kawai, Akiyoshi, et al., Chemical Modification of Ansamitocins. III. Synthesis and Biological Effects of 3-Acyl Esters of Maytansinol, Chem. Pharm., Bull., 1984, Chem. Pharm. Bull., pp. 3441-3451, vol. 32, No. 9.
Kupchan, S.M., et al., Maytansine, a novel antileukemic ansa macrolide from Maytenus ovatus, J. Am. Chem. Soc., 1972, pp. 1354-1356, vol. 94, No. 4.

(Continued)

*Primary Examiner* — Misook Yu
*Assistant Examiner* — Kauser Akhoon
(74) *Attorney, Agent, or Firm* — Buchanan, Ingersoll & Rooney PC

(57) ABSTRACT

Disclosed herein are anti-ERB B2/NEU antibodies conjugated with maytansinoid drugs for targeted delivery to disease tissues. Methods relating to the preparation and uses of such drug conjugates to treat ERB B2/NEU positive cells in cancers are provided.

2 Claims, 6 Drawing Sheets

(56) References Cited

OTHER PUBLICATIONS

Mossner, Ekkehard, et al., Increasing the efficacy of CD290 antibody therapy through the engineering of a new type II anti-CD20 antibody with enhanced direct and immune effector cell-mediated B-cell cytotoxicity, Blood, Jun. 3, 2010, pp. 4393-4402, vol. 115, No. 22.
Nisonoff, A., et al., Separation of Univalent Fragments from the Bivalent Rabbit Antibody Molecule by Reduction of Disulfide Bonds, 1960, pp. 230-244, Archives of Biochemistry and Biophysics 89.
O'Keefe, Donald O., et al., Characterization of a Transferrin-Diphtheria Toxin Conjugate, The Journal of Biological Chemistry, 1985, pp. 932-937, vol. 260, No. 2, American Society of Biological Chemists, Inc.
Parham, Peter, On the Fragmentation of Monoclonal IgG1, IgG2a, and IgG2b from BALB/c Mice, The Journal of Immunology, Dec. 1983, pp. 2895-2902, vol. 131, No. 6, American Association of Immunologists.
Smith, C.R. Jr., et al., Alkaloids, 1984, ed. Pelletier, S.W., 2, pp. 149-204, Wiley, NY.
Remillard, Stephen et al., Antimitotic Activity of the Potent Tumor Inhibitor Maytansine, Science, Sep. 1975, pp. 1002-1005, vol. 189, Dept. of Biology, University of Virginia.
Spring, Susan B., et al., The Journal of Immunology, Aug. 1974, pp. 470-478, vol. 113, No. 2, The Williams & Wilkins Co.
Stanfield, Robyn L., et al., Crystal Structure of a Shark Single-Domain Antibody V Region in Complex with Lysozyme, Science, Sep. 17, 2004, pp. 1770-1773, vol. 305, www.sciencemag.org.
Stewart, Ross, et al., A variant human IgGI-Fc mediates improved ADCC, Protein Engineering, Design & Selection, May 18, 2011, pp. 671-678, vol. 24, No. 9, Oxford University Press, doi:10.1093/protein/gzr015.
Widdison, Wayne C., et al., Semisynthetic Maytansine Analogues for the Targeted Treatment of Cancer, J. Med. Chem., J. Med. Chem., 2006, pp. 4392-4408, vol. 49, American Chemical Society.
Wolpert-Defilippes, Mary K., et al., Initial Studies on Maytansine-Induced Metaphase Arrest in L1210 Murine Leukemia Cells, Biochemical Pharmacology, 1975, pp. 1735-1738, vol. 24, Pergamon Press, Great Britain.
Wood, Clive R., et al., High Level Synthesis of Immunoglobulins in Chinese Hamster Ovary Cells, Journal of Immunology, Nov. 1, 1990, pp. 3011-3016, vol. 145, No. 9, American Assn. of Immunologists.
Yu, Tin-Wein, et al., The biosynthetic gene cluster of the maytansinoid antitumor agent ansamitocin from Actinosynnema pretiosum, PNAS, Jun. 11, 2002, pp. 7968-7973, vol. 99, No. 12, www.pnas.org/cgi/doi/10.1073/pnas.092697199.
Vippagunta et al. "Crystalline Solids," Advanced Drug Delivery Reviews, 2001, 48, pp. 18.
Braga et al.; Stuct. Bond. 2009, 132, 25-50.
U.S. Appl. No. 15/082,697, filed Mar. 28, 2016, Bio-Thera Solutions, Ltd., Co.
U.S. Appl. No. 15/606,648, filed May 26, 2017, Bio-Thera Solutions, Ltd., Co.
Alley et al., "Contribution of Linker Stability to the Activities of Anticancer lmmunoconjugates," 19 Bioconjugate Chem. 759-65 (2008).
Decision on Appeal No. 2015-002728 issued in U.S. Appl. No. 13/297,408, dated Nov. 10, 2016.

* cited by examiner

COMPOUNDS AND METHODS FOR THE TREATMENT OF ERB B2/NEU POSITIVE DISEASES

CROSS REFERENCE TO RELATED APPLICATIONS

This application is a divisional application of U.S. application Ser. No. 13/837,187, filed Mar. 15, 2013, which claims priority under 35 U.S.C. §119 to CN 201210563916.9, filed on Dec. 21, 2012 and CN 201310081880.5, filed on Mar. 14, 2013, the contents of which are hereby expressly incorporated by reference in their entirety for all purposes and are assigned to the assignee hereof.

FIELD OF INVENTION

The present invention generally relates to compounds comprising antibodies, antigen-binding fragments thereof, polypeptides, and immunoconjugates that bind to ERB B2/NEU (HER2). The present invention also relates to methods of using such ERB B2/NEU-binding molecules for diagnosing and treating diseases, such as malignancies.

BACKGROUND OF INVENTION

The ErbB2/NEU (HER2) receptor is amplified and overexpressed in 20% to 25% of human breast cancer and also predictive of poor clinical outcome, ErbB2/NEU (HER2) receptor was recognized and validated for targeted antibody therapy. Trastuzumab (Herceptin), a humanized anti-ErbB2/NEU receptor antibody was approved by the Food and Drug Administration in 1998 for use in metastatic breast cancer and later on for gastric cancer. Despite the clinical benefits, a significant proportion of patients treated with trastuzumab either do not respond initially or relapse after experiencing a period of clinical response. There is need to develop more efficacious therapy. Direct covalent coupling of cytotoxic agents to monoclonal antibodies is an alternative to naked antibody-targeted therapy. Trastuzumab has been conjugated with maytansine and tested in human clinical trials. However, it is known that different linkers, and the methods by which the linkers are conjugated with the antibody impact the efficacy and safety of the drug antibody conjugates.

Maytansinoids are highly cytotoxic compounds which inhibit the formation of microtubule protein polymerization (Remillard, et al., Science 189, 1002-1005 (1975)). Maytansine was first isolated by Kupchan et al. (J. Am. Chem. Sci 94:1354-1356 (1972)) from the east African shrub *Maytenus serrata*. Maytansinoids including maytansinol and C-3 esters of maytansinol were also produced by certain microbes (U.S. Pat. No. 4,151,042). Various analogues of maytansinol with different cytotoxicity have also been prepared by synthetic chemistry (for review see Chem. Pharm. Bull. 52 (1) 1-26 (2004)). Examples of mytansinoids include maytansine, mertansine (MD1), MD3 and MD4. Maytansine is a strong mitotic inhibitor and shows significant inhibitory activity against multiple tumors including Lewis lung carcinoma and B-16 melanocarcinoma solid murine tumor models. Maytansine was reported to inhibit the human acute lymphoblastic leukemia line C.E.M. at concentrations as low as $10^{-7}$ □g/mL (Wolpert-DeFilippes et al., Biochem. Pharmacol. 1735-1738 (1975)). It also showed to be 100- to 1000-fold more cytotoxic than conventional chemotherapeutic agents like methotrexate, daunorubicin, and vincristine (U.S. Pat. No. 3,896,111).

Ansamitocins, the bacterial maytansinoids, show an activity spectrum and effective dosage range similar to maytansine. They inhibit P388 leukemia at daily doses as low as 0.8 □g/kg. Ansamitocin P3 (AP3) was also shown to be effective against multiple cancer cell lines (for review see Alkaloids, vol. 2, 149-204 (1984); Chem. Pharm. Bull. 52 (1) 1-26 (2004)). The maytansinol C-3 esters with N-methyl-L-alanine derivatives are found to be much more cytotoxic than the corresponding esters of simple carboxylic acid and to be 100 times more cytotoxic than their epimers corresponding to N-methyl-D-alanine (U.S. Pat. Nos. 4,137,230; 4,260,608; Kawai, et al., Chem. Pharm. Bull. 32: 3441-3451 (1984); Widdison, et al., J. Med. Chem. 49: 4392-4408 (2006)).

Maytansinoids were expected to have the capacity to treat many different cancers due to their highly toxic nature and the in vitro activities against multiple cancer cell lines. However, the toxicity also made this class of compounds not favorable in human clinical trials as the side effects were intolerable for many patients (Issel et al., 5 Cancer Treat. Rev. 199-207 (1978)). Accordingly, targeted delivery of cytotoxic compounds to cancer cells by conjugating toxic drugs to monoclonal antibodies (ADC for antibody drug conjugate) is proposed in order to reduce the side effects. Certain conjugates of cytotoxic drugs such as maytansinoids, auristatins, anthracyclins, duocarmycins, etc. with antibodies are being evaluated in preclinical or clinical studies in the treatment of diseases.

Antibody drug conjugates (ADCs) are composed of three key elements: antibody, linker, and drug. The selection of a particular antibody and drug will have a great impact on the efficacy and safety depending on the particular disease. Linker stability and the method by which the drug is conjugated to the antibody plays a critical role in the success or failure of the ADC drug development.

The efficacy of an ADC depends in part on combination of a variety of parameters, involving not only the specificity of the antibody and the potency of drugs, but also the linker's stability or sensitivity to cleavage, the cell surface triggered the internalization, trafficking, and subsequent release of the active cytotoxic payload. Thus, ADC comprising different drug linkers or with different antibodies against the same target can vary significantly in their utility.

SUMMARY OF THE INVENTION

The present invention provides an anti-Erb B2/neu antibody that is conjugated with maytansinoid molecules, thus targeting disease cells or tissues. The anti-Erb B2/neu antibody binds to an antigen in the disease cells or tissues. A drug conjugated to the antibody exerts a cytotoxic, cytostatic, or immunosuppressive effect on the antigen-expressing cells to treat or prevent recurrence of ERB B2/NEU-positive cancers. The high affinity of the antibody drug conjugate ensure that the cytotoxic maytansinoid targets the tumor cells. Otherwise, the highly toxic maytansinoid will become systemically bound to unintended targets which results in very high and often unacceptable toxicity. The present technology provides a method to treat cancers by exerting cellular inhibitory or killing effect of maytansinoid on the ERB B2/NEU positive cells, while minimizing the undesirable side effects of maytansinoid, such as bystander killing effects on antigen negative cells.

In one aspect, provided is an anti-Erb B2/neu antibody conjugated with a maytansinoid compound, wherein the maytansinoid compound is d linked to an anti-Erb B2/neu antibody via a linker that is not acid labile, not peptidase cathepsin sensitive, and does not contain a disulfide bond and provides stability during circulation while being able to release the drug once inside the cells. Such linkers are contemplated to provide stability to the conjugated molecule prior to endocytosis, such as during circulation, to prevent premature degradation of the linker and release of the toxic drug, thus minimize the toxic effect of the drug. In some embodiments, the maytansinoid-linker portion of the conjugate is N2'-deacetyl-N2'-(6-maleimido-1-oxo-hexyl)-maytansine (3AA-MDC or batansine), or a derivative thereof. In some embodiments, the conjugate has a high drug load of at least 3 drug molecules per antibody for improved activity. Surprisingly, the antibody remain sufficiently stable for targeted delivery of the drug to target cells despite the high drug load.

In some embodiments, provided herein is a maytansinoid linker anti-Erb B2/neu antibody conjugate of Formula Ia or Ib:

n is 0, 1, 2, 3, 4, 5, 6, 7 or 8;
p is selected from 3, 4, 5, 6, 7, 8, 9, 10; and
Anti-HER2 is anti-ERB B2/NEU antibody.

In another aspect, provided is a composition comprising the above-described maytansinoid linker anti-Erb B2/neu antibody conjugate, such as a compound of Formula Ia.

In another aspect, provided is a method of preparing the above-described maytansinoid linker anti-Erb B2/neu antibody conjugate which method comprises contacting an anti-Erb B2/neu antibody with one or more maytansinoid compounds described herein capable of being conjugated to the anti-Erb B2/neu antibody.

In another aspect, provided is a method for targeting a maytansinoid to ERB B2/NEU antigen positive cells or

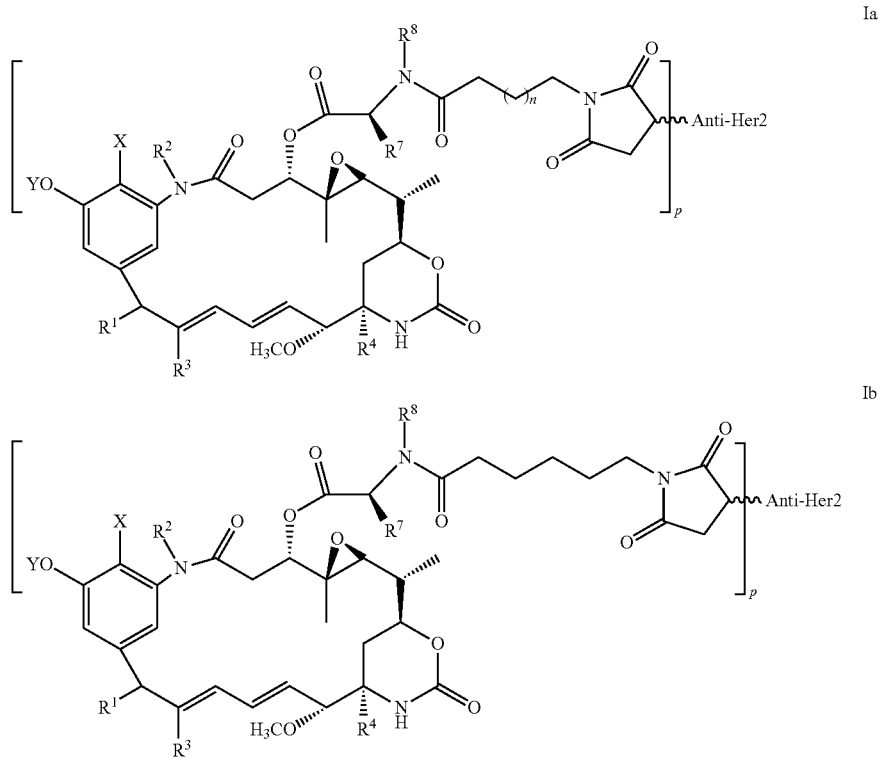

or a pharmaceutically acceptable salt or solvate thereof, wherein

X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;

tissues with an anti-Erb B2/neu antibody conjugated with maytansinoids described herein.

In some embodiments, the anti-Erb B2/neu antibody has an amino acid sequence comprising the amino acid sequences of trastuzumab or pertuzumab, or an equivalent thereof.

In another aspect, provided is a method for treatment of proliferative disorders such as tumors, inflammatory or immunologic diseases such as graft rejections, and other diseases that can be treated by targeted therapy in a subject in need of the treatment, wherein the disease is characterized by cells comprising an antigen that binds to an anti-Erb B2/neu antibody, said method comprising administering to the subject an effective amount of the anti-Erb B2/neu antibody drug conjugate described herein.

DETAILED DESCRIPTION OF THE INVENTION

Definitions

Figure 1:
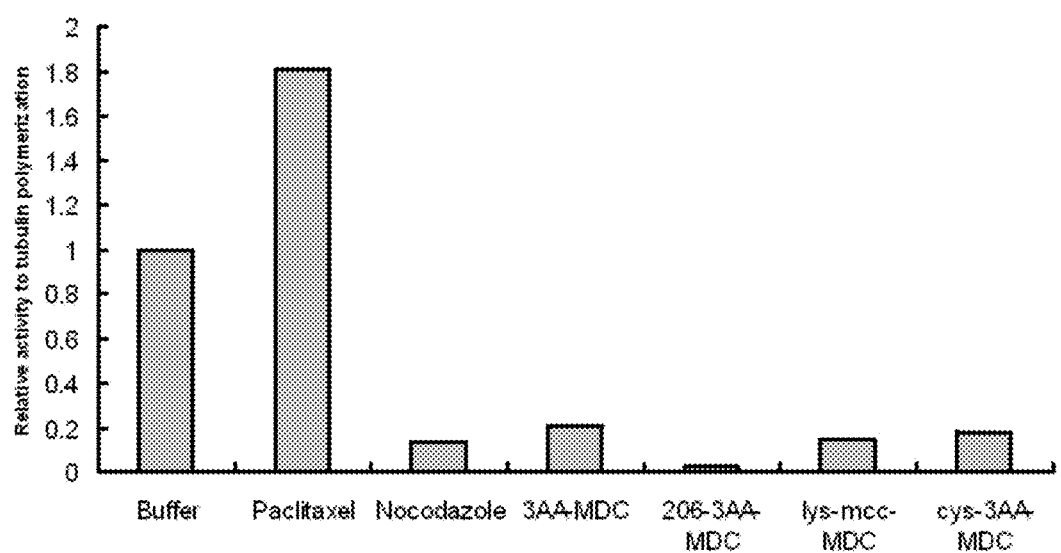
FIG. 1 shows the effects of 3AA-MDC (the linkered drug N2'-deacetyl-N2'-(6-maleimido-1-oxo-hexyl) maytansine) and related metabolites on the tubulin polymerization.

As used herein, the following definitions shall apply unless otherwise indicated.

As used herein, unless otherwise stated, the singular forms "a," "an," and "the" include plural reference. Thus, for example, a reference to "a compound" includes a plurality of compounds.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% or plus or minus 5%, or plus or minus 1% of the particular term.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, "maytansinoid" refers to a maytansine analogue, including stereoisomers thereof. Maytansine can be isolated from plants of the genus Maytenus U.S. Pat. No. 3,896,111). It is of the formula:

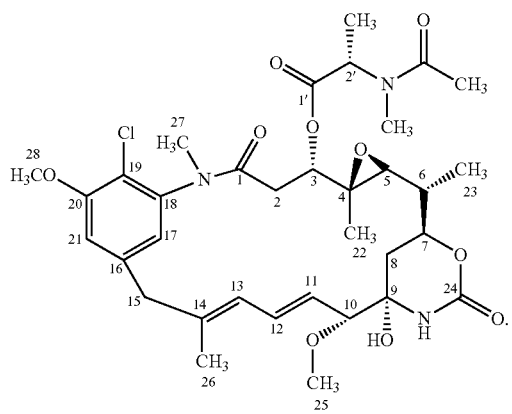

Maytansinoids are compounds having the ring structure of maytansine with one or more modifications of the substituents on the ring.

"Alkyl" refers to monovalent saturated aliphatic hydrocarbyl groups having from 1 to 10 carbon atoms and preferably 1 to 6 carbon atoms. $C_v$ alkyl wherein v is an integer represents an alkyl having v carbons. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). "Alkylene" is a divalent saturated aliphatic hydrocarbyl groups having from 1 to 10 carbon atoms and preferably 1 to 6 carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH).

"Amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' and R" is hydrogen but not both. When referring to a disubstituted amino, it is meant that neither R' and R" are hydrogen.

"Amino acid" refers any compound, whether natural, unnatural or synthetic, which includes both an amino group and a carboxy group. Examples of amino acid include, but are not limited to glycine ($NH_2CH_2COOH$), cysteine, alanine, N-methyl-L-alanine, including both the D and L optical isomers. "Amino acid side chain" refers to the substituent that replaces a hydrogen of the methylene group of glycine or glycine derivatives, such as N-alkylglycine or glycine esters. Examples of an amino acid side chain include, but are not limited to the side chains of the natural amino acids, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Carbonyl" refers to the divalent group —C(O)— which is equivalent to —C(=O)—.

"Carboxy" or "carboxyl" refers to —COOH or $CO_2H$ or salts thereof.

"Carboxylic acid" refers to a compound having at least one carboxy.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5]dec-8-yl:

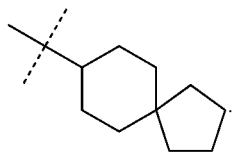

Cycloalkylene refers to a cyclic alkylene.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Substituted alkyl," "substituted alkenyl," "substituted alkynyl," "substituted cycloalkyl," "substituted cycloalkenyl," "substituted aryl," "substituted heteroaryl" or "substituted heterocyclic" refers to alkyl, alkenyl, alkynyl, cycloalkyl, cycloalkenyl, aryl, heteroaryl or heterocyclic groups, respectively, which are substituted with 1 to 5, preferably 1 to 3, or more preferably 1 to 2 substituents selected from the group consisting of alkyl, halo alkyl, —O—$R^{20}$, —S—$R^{20}$, alkenyl, alkynyl, —C(=O)$R^{20}$, —C(=S)$R^{20}$, —C(=O)O$R^{20}$, —$NR^{20}$(=O)$R^{21}$, —OC(=O)$R^{21}$, —$NR^{20}R^{20}$, —C(=O)$NR^{20}R^{20}$, —C(=S)$NR^{20}R^{20}$, —$NR^{20}$C(=O)$NR^{20}R^{20}$, —$NR^{20}$C(=S)$NR^{20}R^{20}$, —OC(=O)$NR^{20}R^{20}$, —$SO_2NR^{20}R^{20}$, —$OSO_2NR^{20}R^{20}$, —$NR^{20}SO_2NR^{20}R^{20}$, —C(=$NR^{20}$)$NR^{20}R^{20}$, aryl, —$NR^{20}$C(=O)$OR^{21}$, —OC(=O)$OR^{21}$, cyano, cycloalkyl, cycloalkenyl, —$NR^{20}$C(=$NR^{20}$)$NR^{20}R^{20}$, halo, hydroxy, heteroaryl, heterocyclic, nitro, —$SO_3H$, —$SO_2R^{21}$, and —$OSO_2R^{21}$, wherein each $R^{20}$ is selected from the group consisting of hydrogen, alkyl, alkenyl, alkynyl, aryl, cycloalkyl, cycloalkenyl, heteroaryl, and heterocyclic or two $R^{20}$ with the atom(s) bound thereto form a heterocyclic ring, and $R^{21}$ is selected from the group consisting of alkyl, alkenyl, alkynyl, aryl, cycloalkyl, cycloalkenyl, heteroaryl, and heterocyclic.

"Nitro" refers to the group —NO$_2$.

"Oxo" refers to the atom (=O) or (—O).

"Spiro ring systems" refers to bicyclic ring systems that have a single ring carbon atom common to both rings.

"Thiol" refers to the group —SH.

"Thiocarbonyl" refers to the divalent group —C(S)— which is equivalent to —C(=S)—.

"Thione" refers to the atom (=S).

"Compound" or "compounds" as used herein is meant to include the stereoiosmers and tautomers of the indicated formulas.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Solvate" refer to an association of a solvent with a compound, in the crystalline form. The solvent association is typically due to use of the solvent in the synthesis, crystallization, and/or recrystallization of the compound. "Solvate" includes hydrate which is an association of water with a compound, in the crystalline form.

"Patient" or "subject" refers to mammals and includes humans and non-human mammals.

"Pharmaceutically acceptable salt" refers to pharmaceutically acceptable salts of a compound, which salts are derived from a variety of organic and inorganic counter ions well known in the art and include, by way of example only, when the molecule contains an acidic functionality, salts of organic or inorganic bases, such as sodium, potassium, calcium, magnesium, ammonium, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and tetraalkylammonium, and the like; and when the molecule contains a basic functionality, salts of organic or inorganic acids, such as hydrochloride, hydrobromide, tartrate, mesylate, acetate, maleate, and oxalate. Other non-limiting examples of acids include sulfuric acid, nitric acid, phosphoric acid, propionic acid, glycolic acid, pyruvic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease.

"Effective amount" is intended to mean an amount of an active compound or pharmaceutical agent that elicits the biological or medicinal response in a tissue, system, animal, individual or human that is being sought by a researcher, veterinarian, medical doctor or other clinician, which includes treating a disease.

Anti-Erb B2/neu Antibody Drug Conjugates

In one aspect, disclosed herein is a maytansinoid conjugated to an anti-ERB B2/NEU antibody via a linker that is not acid labile, not peptidase cathepsin sensitive, and that is stable in circulation while being able to release the cytotoxic drug inside the cells and with a high drug load of at least 3 drug molecules per antibody.

Maytansinoids suitable for attaching the linking group include maytansinol and maytansinol analogues and can be isolated from natural sources according to known methods, produced using biotechnologies (see e.g., Yu et al., 99 PNAS 7968-7973 (2002)), or prepared synthetically according to known methods (see e.g., Cassady et al., Chem. Pharm. Bull. 52 (1) 1-26 (2004)).

Certain examples of suitable maytansinol analogues include:

(1) C-19-dechloro (U.S. Pat. No. 4,256,746) (prepared by LAH reduction of ansamytocin P2);

(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using lithium aluminium hydride (LAH));

(3) C-20-demethoxy, C-20-acyloxy (—OCOR), +/−dechloro (U.S. Pat. No. 4,294,757) (prepared by acylation using acyl chlorides);

(4) C-9-SH (U.S. Pat. No. 4,424,219) (prepared by the reaction of maytansinol with H$_2$S or P$_2$S$_5$);

(5) C-14-hydroxymethyl (CH$_2$OH) or acyloxymethyl (CH$_2$OC(=O)phenyl or CH$_2$OC(=) (C$_1$-C$_5$ alkyl)) (U.S. Pat. No. 4,331,598) (prepared from *Nocardia*);

(6) C-15-hydroxy/acyloxy (U.S. Pat. No. 4,364,866) (prepared by the conversion of maytansinol by *Streptomyces*);

(7) C-15-methoxy (U.S. Pat. Nos. 4,313,946 and 4,315,929) (isolated from *Trewia nudlflora*);

(8) C-18-N-demethyl (U.S. Pat. Nos. 4,362,663 and 4,322,348) (prepared by the demethylation of maytansinol by *Streptomyces*); and (9) 4,5-deoxy (U.S. Pat. No. 4,371,533) (prepared by the titanium trichloride/LAH reduction of maytansinol).

Many positions on maytansinol can be useful as the linkage position, depending upon the type of linker. For example, for forming an ester linkage, the C-3 position having a hydroxyl group, the C-14 position modified with hydroxymethyl, the C-15 position modified with a hydroxyl group and the C-20 position having a hydroxyl group are all suitable. In some embodiments, the linkage position is the C-3 position.

In some embodiments, provided is a compound of Ia or Ib

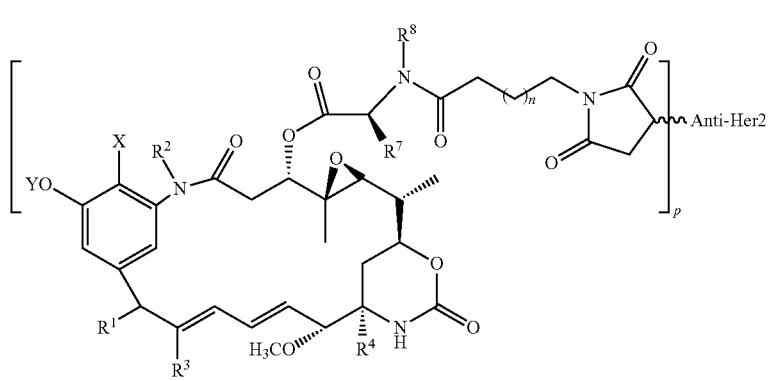

Ia

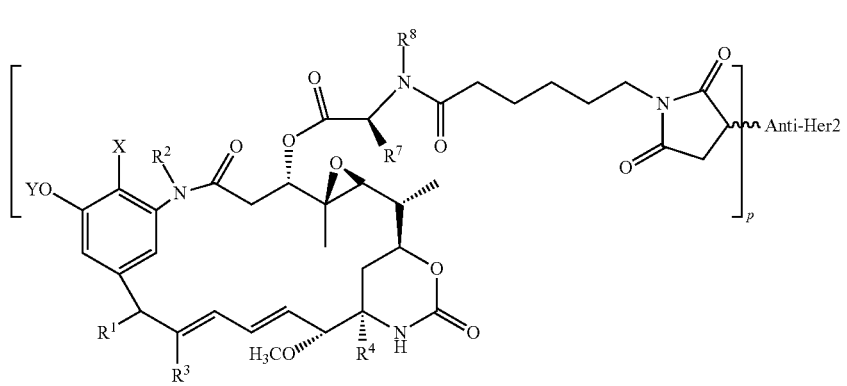

Ib or a pharmaceutically acceptable salt or solvate thereof, wherein
- X is hydrogen or halo;
- Y is selected from the group consisting of hydrogen, $C_1$-$C_6$ alkyl, $C_3$-$C_6$ cycloalkyl, and —C(=O)$R^5$;
- $R^1$ is selected from the group consisting of hydrogen, —OH, —OC(=O)$R^5$ and —O$R^5$;
- $R^2$ is hydrogen or $C_1$-$C_6$ alkyl;
- $R^3$ is methyl, —CH$_2$OH, or —CH$_2$C(=O)$R^6$;
- $R^4$ is —OH or —SH;
- $R^5$ is $C_1$-$C_6$ alkyl or benzyl;
- $R^6$ is $C_1$-$C_6$ alkyl, phenyl or benzyl;
- $R^7$ is hydrogen, $C_1$-$C_6$ alkyl or an amino acid side chain;
- $R^8$ is hydrogen or $C_{1-6}$ alkyl;
- n is 0, 1, 2, 3, 4, 5, 6, 7 or 8;
- p is selected from 3, 4, 5, 6, 7, 8, 9, 10; and
- Anti-HER2 is anti-ERB B2/NEU antibody.

In some embodiments, the compound of Ia is

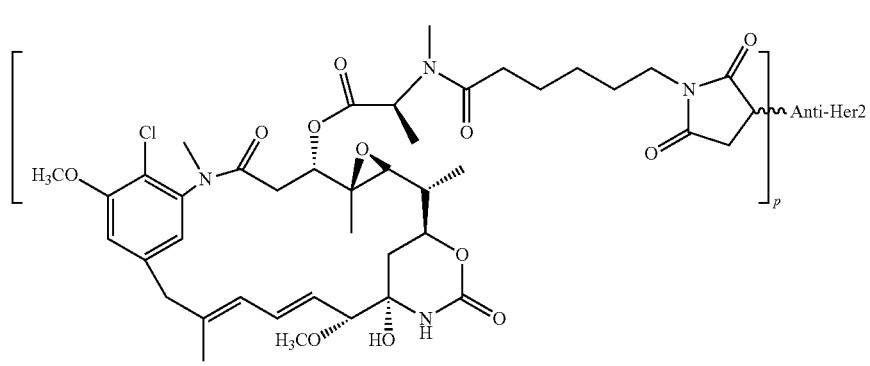

Ic or a pharmaceutically acceptable salt or solvate thereof, wherein Anti-Her2 is anti-ERB B2/NEU (HER2) antibody.

In some embodiments, the anti-Her2 antibody is trastuzumab or an equivalent thereof.

The maytansinoid component of the maytansinoid derivatives having a linking group capable of conjugating to an anti-Erb B2/neu antibody or the maytansinoid linker anti-Erb B2/neu antibody conjugates can be substituted by other suitable cytotoxic agents, for example, an auristatin, a DNA minor groove binding agent, a DNA minor groove alkylating agent, an enediyne, a lexitropsin, a duocarmycin, a taxane, a puromycin, a dolastatin, and a vinca alkaloid. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. In some embodiments, the cytotoxic agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-3, DM-4, or eleutherobin. Suitable immunosuppressive agents include, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist. In some embodiments, the cytotoxic agent is AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, DM-3, DM-4, or netropsin.

The maytansinoid component of the maytansinoid derivatives having a linking group capable of conjugating to an anti-Erb B2/neu antibody and the maytansinoid linker anti-Erb B2/neu antibody conjugates can also be substituted by a suitable immunosuppressive agent, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist.

Anti-Erb B2/neu Antibody

Anti-Erb B2/neu antibody include ragments of antibodies (polyclonal and monoclonal) such as Fab, Fab', F(ab')$_2$, and Fv (see, e.g., Parham, J. Immunol. 131:2895-2902 (1983); Spring et al., J. Immunol. 113:470-478 (1974); Nisonoff et al., Arch. Biochem. Biophys. 89:230-244 (1960)); domain antibodies (dAbs) and antigen-binding fragments thereof, including camelid antibodies (see, e.g., Desmyter et al., Nature Struct. Biol, 3:752 (1996)); shark antibodies called new antigen receptors (IgNAR) (see, e.g., Greenberg et al., Nature, 374:168 (1995); Stanfield et al. Science 305:1770-1773 (2004)).

Monoclonal antibody techniques allow for the production of anti-Erb B2/neu antibody in the form of specific monoclonal antibodies. Particularly well known in the art are techniques for creating monoclonal antibodies produced by immunizing mice, rabbits, or any other mammal with the antigen of interest such as the tumor specific antigens isolated from the target cell. Another method of creating anti-Erb B2/neu antibody is using phage libraries of scFv (single chain variable region), specifically human scFv (see, e.g., Griffiths et al., U.S. Pat. Nos. 5,885,793 and 5,969,108; McCafferty et al., WO 92/01047; Liming et al., WO 99/06587), or domain antibodies using yeast selection system (see, e.g., U.S. Pat. No. 7,195,595). In addition, resurfaced antibodies such as those disclosed in U.S. Pat. No. 5,639,641 may also be used, as may chimerized or humanized antibodies.

Selection of a particular anti-Erb B2/neu antibody is a matter of choice that depends upon the disease type, cells and tissues that are to be targeted.

In some embodiments, the anti-Erb B2/neu antibody is human monoclonal antibody.

Anti-Erb B2/neu antibodies that have specificity to a tumor antigen can be used. A "tumor antigen" as used herein, refers to an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

Anti-Erb B2/neu antibody having specificity to a protein that is overexpressed on a tumor cell as compared to a corresponding non-tumor cell can also be used. ERB B2/NEU is highly expressed in a range of solid tumors including those of the breast and stomach.

It is contemplated that anti-Erb B2/neu antibody can be modified to introduce an amino acid sequence having improved antibody-dependent cellular cytotoxicity (ADCC). For instance, amino acids in the Fc and/or hinge region can be modified to achieve improved ADCC. Examples of IgG1-Fc that mediates improved ADCC, as well as methods of screening for such sequences, are known in the art (e.g., Stewart et al. Protein Eng Des Sel. 24 (9):671-8, 2011).

Conjugation of a Drug to an Anti-Erb B2/neu Antibody

As discussed, a drug (e.g., a maytansinoid drug derivative) can be conjugated to an anti-Erb B2/neu antibody through a linker. In one embodiment, the anti-Erb B2/neu antibody can be modified with appropriate bifunctional modifying agent. In some embodiments, a group comprising a thiol (SH) group (also referred to as thio-comprising group) can be introduced to the side-chain of an amino acid residue, such as the side-chain of a lysine, on the anti-Erb B2/neu antibody. For example, the amino group of a lysine residue on the anti-Erb B2/neu antibody can be converted to a thiol-comprising group by reaction with 2-iminothiolane (Traut's Reagent), or with N-succinimidyl 3-(2-pyridyldithio)propanoate (SPDP), N-succinimidyl 4-(2-pyridyldithio) butanoate (SPDB), etc and followed by reduction with a reducing reagent, such as 2-mercaptoethanol, dithiothreitol (DTT) or tris(2-carboxyethyl)phosphine (TCEP).

Non-limiting examples of thiol-comprising group that can replace the side-chain amino group of a lysine residue include —NHC(=NH)(CH$_2$)$_n$SH and —NHC(O)(CH$_2$)$_n$SH, wherein n is 1, 2, 3, 4, 5 or 6. When a thiol-comprising group is introduced to an amino acid residue, the amino acid residue is referred to as thiolated amino acid. For example, when the side-chain amino group of a lysine residue is converted to a thio-comprising group, the lysine residue is referred to as thiolated lysine. The number of free thiol (SH) group introduced in an anti-Erb B2/neu antibody may vary, such as between 1 and about 20, or 5 to 15, and or 5 to 12. The linkers or drug-linkers can form bonds with the free thiol (SH) group of a thiolated lysine residue on the anti-Erb B2/neu antibody. In some embodiments, the number of linkers or drug-linkers that form bonds with thiolated lysine residues in the anti-Erb B2/neu antibody is between 1 and about 10. In some embodiments, the number of such formed bonds is at least 1, or alternatively at least 2, or 3, or 4, or 5. In some embodiments, the number of such formed bonds is no more than 10, or alternatively no more than 9, or 8, 7, 6, 5, or 4. In some embodiments, each anti-Erb B2/neu antibody, on average, is conjugated with 3-5 drug molecules.

In another embodiment, a drug-linker can be conjugated to an anti-Erb B2/neu antibody by binding to the thiol group of a cysteine residue. Each anti-Erb B2/neu antibody typically contains multiple cysteines, but many, if not all, of them form disulfite bonds between each other, and thus are not available for such conjugation. In some embodiments, therefore, one or more of the disulfite bonds of the anti-Erb B2/neu antibody can be broken to form free thiol (SH) groups by reaction with a reducing reagent, such as 2-mercaptoethanol, dithiothreitol (DTT) or tris(2-carboxyethyl) phosphine (TCEP), for instance. The reaction can be monitored and/or controlled so that a sufficient number of disulfite bonds are broken to allow conjugation while maintaining a sufficient number of disulfide bonds to keep the structure stability of the anti-Erb B2/neu antibody.

In some embodiments, the number of bonds formed between the drug-linker and cysteine residue on the anti-Erb B2/neu antibody is from 3 to 10. In one embodiment, the number of such bonds is at least 3, or alternatively at least 4, or 5. In some embodiments, the number of such formed bonds is no more than 10, or alternatively no more than 9, or 8, 7, 6, 5, or 4. In one embodiment, each anti-Erb B2/neu antibody, on average, is conjugated with 3-5 drug molecules through cysteines.

In some embodiments, drug molecules are conjugated to the anti-Erb B2/neu antibody through a mixture of lysine and cysteine residues.

An anti-Erb B2/neu antibody can be modified, by way of, e.g., site-specific mutagenesis, to introduce additional thiolated lysine or cysteine residues to allow suitable conjugation. Amino acid modification methods are well known in the art. Modified anti-Erb B2/neu antibody can then be experimentally examined for their stability and antigen binding capability. In one embodiment, at least one thiolated lysine or cysteine residue is introduced by such modification. In another embodiment, at least two thiolated lysine or cysteine residues are introduced by such modification.

Drug Load

The drug load on an anti-Erb B2/neu antibody may vary depending on many factors, such as the potency of the drug, the size, stability of the anti-Erb B2/neu antibody, conjugatable groups available on the anti-Erb B2/neu antibody, etc. In some embodiments, 1 to 10 maytansinoid drug molecules are conjugated with 1 anti-Erb B2/neu antibody molecule. In some embodiments, an average of 3 to 5 maytansinoid drug molecules are conjugated with 1 anti-Erb B2/neu antibody molecule. In some embodiments, an average of 3.5 maytansinoid drug molecules are conjugated with 1 anti-Erb B2/neu antibody molecule.

Metabolites of Maytansinoids-Linker-Anti-Erb B2/neu Antibody Conjugates to Release the Effective Agents While not wishing to be bound to any theories, it is contemplated that upon endocytosis, compounds of any one of Formula Ia-Ic is degraded by intracellular proteins to metabolites comprising the maytansinoid moiety which are cytotoxic. In some embodiments, the compound is of Formula IVa, IVb or IVc:

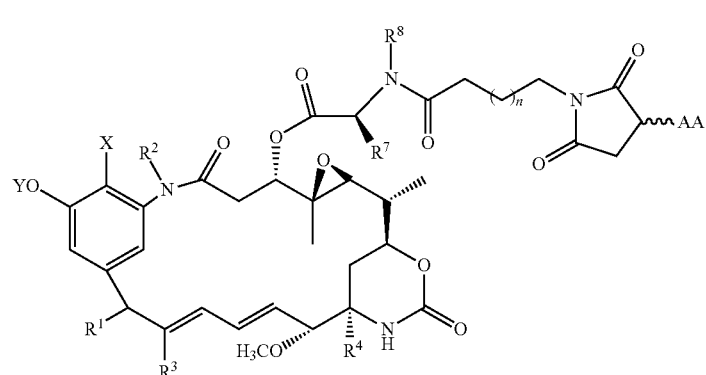

IVa

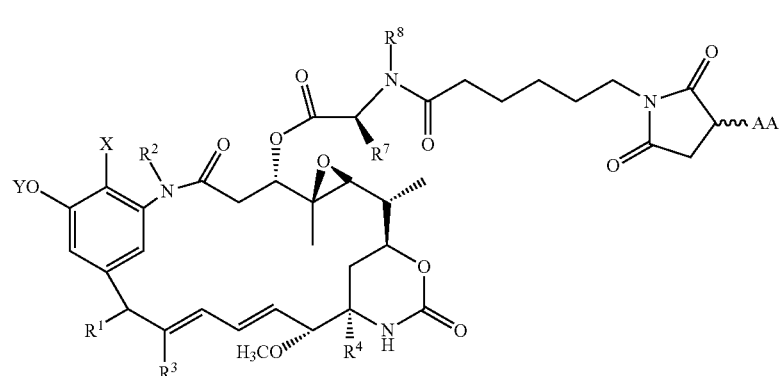

IVb

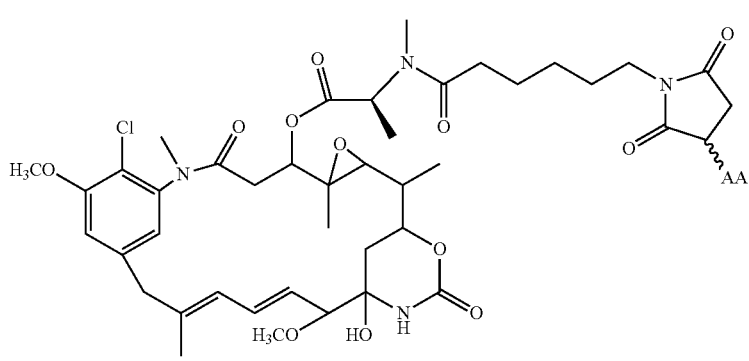

or a salt thereof, wherein AA is selected from, but is not limited to

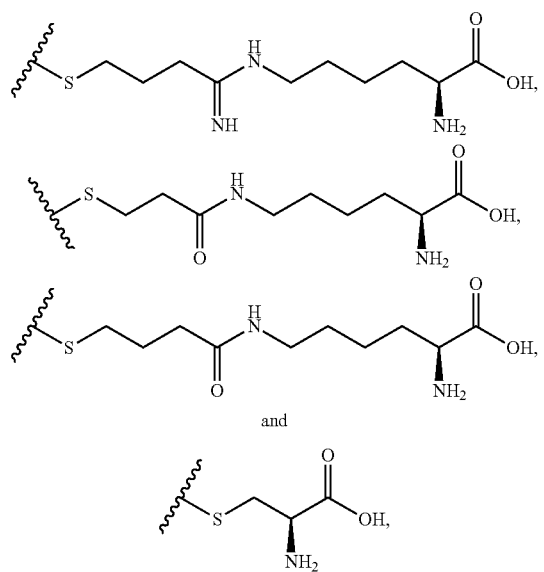

and wherein ⌇⌇⌇ represents point of connection to the rest of the molecule, and other variables are as defined herein.

Methods of Treatment

In another aspect, provided herein is a method of treating a proliferative, inflammatory or immunologic disease or condition in a patient in need thereof comprising administering an effective amount of one or more compounds as described herein, for example, a compound of any one of Formula Ia-Ic and IVa-IVc-.

The compounds can be formulated as pharmaceutical compositions and administered to the patient in a variety of forms adapted to the chosen route of administration, i.e., orally or parenterally, by intravenous (I.V.), intramuscular, topical or subcutaneous routes. The amount of the compounds will vary depend on the nature of the drug, linker, drug load, degree of cell surface triggered the internalization, trafficking, and release of the drug, the disease being treated, the conditions of the patient, such as age, gender, weight, etc. and can be determined by methods known to the art, for example, see U.S. Pat. No. 4,938,949, and will be ultimately at the discretion of the attendant physician or clinician.

In general, a suitable dose will be in the range of from about 0.1 to about 200 mg/kg, e.g., from about 0.5 to about 50 mg/kg of body weight I.V. infusion over 30-90 min every 1-4 week for 52 weeks, about 1.0 to about 25 mg/kg of body weight IV infusion over 30-90 min every 1-4 week for 52 weeks, about 1.5 to about 15 mg/kg body weight IV infusion over 30-90 min every 1-4 week for 52 weeks, or in the range of about 1 to 10 mg/kg body weight IV infusion over 30-90 min every 1-4 week. In some embodiments, the dose is from about 1.0 mg to about 100 mg/day, e.g., from about 2 mg to about 5 g per day, about 10 mg to about 1 g per day, about 20 to about 500 mg per day, or in the range of about 50 to 100 mg per day. The compounds can be administered daily, weekly, monthly, such as once a day, every 1-3 weeks, or month. Alternatively, the compounds can be administered in cycles, such as administered daily for a number of days, for example, 5 days to 21 days, with a period, such as one day to seven days, wherein no drug is being administered.

In some embodiments, the compound is administered at an initial dose of 1-4 mg/kg over 30-90 minute IV infusion, followed by 1-2 mg/kg over 30 minute I.V. infusion weekly or every 1-4 weeks for 52 weeks. In some embodiments, the compound is administered at an initial dose of 2-10 mg/kg over 30-90 minutes I.V. infusion, followed by 1-5 mg/kg over 30-90 minutes IV infusion every 1-4 weeks for 52 weeks.

In some embodiments, the compounds are administered in conjunction with another therapy. For example, the compounds can be co-administered with another therapy for treating cancer, for example, radiation therapy or another anticancer agent known in the art.

In another aspect, provided herein is a method of treating a proliferative, inflammatory or immunologic disease or condition in a patient in need thereof comprising administering an effective amount of a compound of Formula IVa, wherein the compound of Formula IVa is generated as a result of a metabolic chemical reaction following administration of a compound of Formula Ia, or a pharmaceutically acceptable salt thereof, to the patient.

In another aspect, provided herein is a method of treating a proliferative, inflammatory or immunologic disease or condition in a patient in need thereof comprising administering an effective amount of a compound of Formula IVb, wherein the compound of Formula IVb is generated as a result of a metabolic chemical reaction following administration of a compound of Formula Ib, or a pharmaceutically acceptable salt thereof, to the patient.

In another aspect, provided herein is a method of treating a proliferative, inflammatory or immunologic disease or condition in a patient in need thereof comprising administering an effective amount of a compound of Formula IVc, wherein the compound of Formula IVc is generated as a result of a metabolic chemical reaction following administration of a compound of Formula Ic, or a pharmaceutically acceptable salt thereof, to the patient.

Metabolic chemical reaction refers to a reaction occurring inside the body, for example, cells, of the subject, in which a chemical compound is converted to another chemical compound. The conversion can be by metabolic and/or chemical processes and can occur in one step or through a series of two or more steps. Metabolic chemical reactions include reactions of degrading a protein or peptide component of a maytansinoid linker anti-Erb B2/neu antibody conjugate, such as an antibody or antibody fragment, by proteins inside a cell.

Pharmaceutical Compositions

In a further aspect, provided are pharmaceutical compositions comprising one or more compounds as described herein, for example, a compound of any one of Formula Ia-Ic, and one or more pharmaceutically acceptable carriers. Such compositions should contain at least 0.1% of active compound. The percentage of the compositions may vary and may be between about 2 to about 90% of the weight of a given unit dosage form. The amount of active compound in such therapeutically useful compositions is such that an effective dosage level will be obtained.

Examples of pharmaceutical compositions suitable for injection or infusion can include sterile aqueous solutions or dispersions in a pharmaceutically acceptable liquid carrier or vehicle, or sterile powders comprising the active ingredient which are adapted for the extemporaneous preparation of sterile injectable or infusible solutions or dispersions, optionally encapsulated in liposomes. Other forms of pharmaceutical compositions include topical formulations, such as gel, ointments, creams, lotions or transdermal patches, etc. The pharmaceutical compositions include using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

In a further aspect, provided are methods of producing a pharmaceutical composition comprising admixing a compound as described herein, for example, a compound of any one of Formula Ia-IVc, and a pharmaceutically acceptable carrier. Methods of admixing an active ingredient with a pharmaceutically acceptable carrier are generally known in the art, for example, uniformly mixing the active compound(s) with liquids or finely divided solid carriers, or both, in the required proportions, and then, if necessary, forming the resulting mixture into a desired shape.

In some embodiments, a compound of any one of Formula Ia-IVc is formulated as an injectable, for example, at a concentration of 2-50 mg/mL in an aqueous solution comprising 4-10 mg/mL sodium chloride and/or 5-12 mg/mL sodium acetate, or alternatively at a concentration of 2-50 mg/mL in an aqueous solution comprising 5-10 mg/mL sodium chloride, 1-5 mg/mL sodium phosphate dibasic heptahydrate, 0.1-0.5 mg/mL sodium phosphate monobasic monohydrate.

Other examples of formulations of a compound of any one of Formula Ia-IVc include an injectable formulation having a concentration of 2-100 mg/mL of the compound in an aqueous solution comprising 0.5-1.0% sodium chloride, 0.05-0.10% monobasic sodium phosphate dihydrate, 1.0-2.0% dibasic sodium phosphate dihydrate, 0.01-0.05% sodium citrate, 0.10-0.20% citric acid monohydrate, 1.0-2.0% mannitol, 0.1%-0.2 polysorbate 80, and Water for Injection, USP. Sodium hydroxide added as necessary to adjust pH.

Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Coupling reagents include carbodiimide, amininum and phosphonium based reagents. Carbodiimide type reagents include dicyclohexylcarbodiimide (DCC), diisopropylcarbodiimide (DIC), and 1-ethyl-3-(3-dimethylaminopropyl)-dicarbodiimide (EDC), etc. Aminium salts include N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU). Phosphonium salts include 7-azabenzotriazol-1-yl-N-oxy-tris(pyrrolidino)phosphonium hexafluorophosphate (PyAOP) and benzotriazol-1-yl-N-oxy-tris(pyrrolidino)phosphonium hexafluorophosphate (PyBOP). Amide formation step may be conducted in a polar solvent such as dimethylformamide (DMF) and may also include an organic base such as diisopropylethylamine (DIEA) or dimethylaminopyridine (DMAP).

For example, compounds of Formula Ia or Ib can be prepared by contacting a compound of Formula A or B, respectively, wherein the variables are as defined herein, with an antibody in a suitable solvent, such as a buffer.

The following examples are provided to illustrate certain aspects of the present invention and to aid those of skill in the art in practicing the invention. These examples are in no way to be considered to limit the scope of the invention.

Example 1

Esterification of Maytansinol with Fmoc-N-methyl-L-alanine (Fmoc-N-Me-D/L-Ala-MDC)

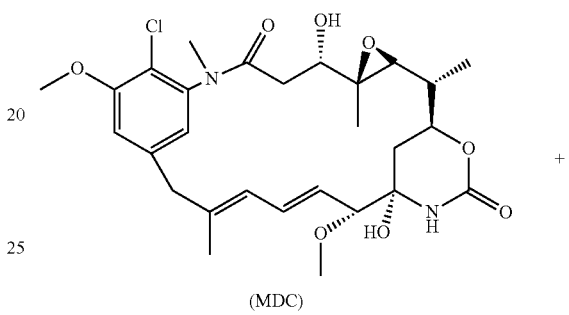

(MDC)

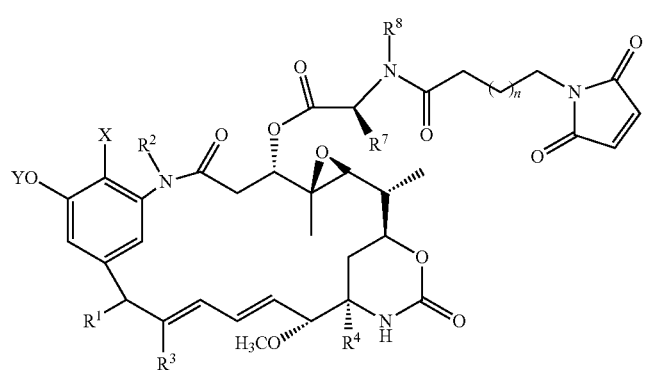

A

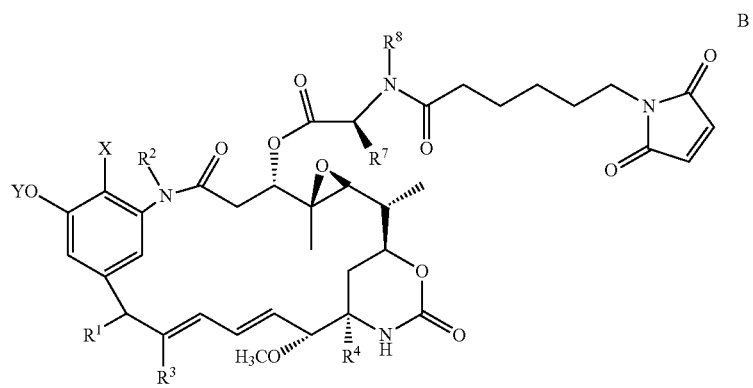

B

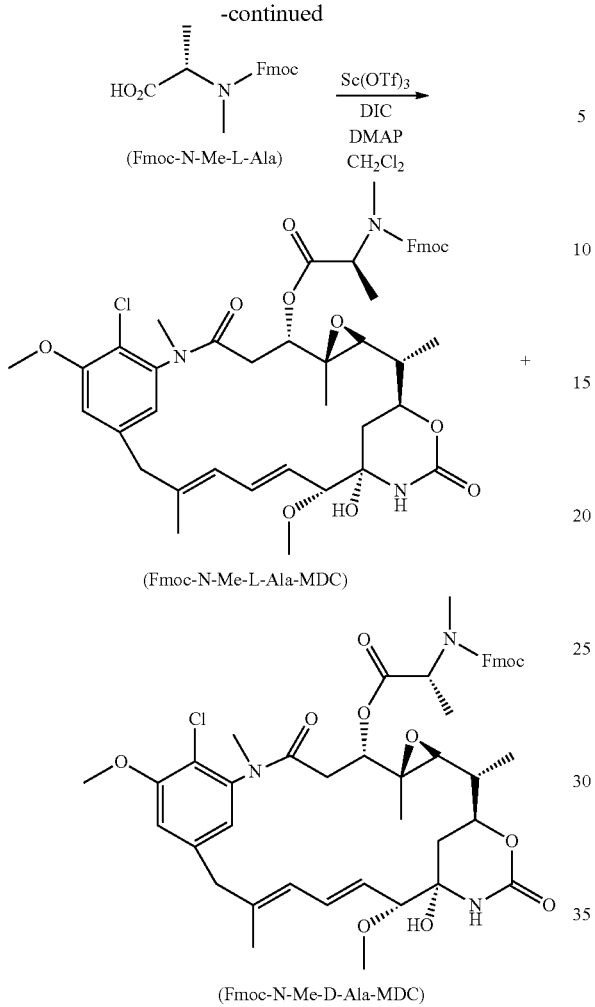

(Fmoc-N-Me-L-Ala)

(Fmoc-N-Me-L-Ala-MDC)

(Fmoc-N-Me-D-Ala-MDC)

A mixture of maytansinol (0.600 g, 1.062 mmol), Fmoc-N-Me-L-Ala (6.911 g, 21.24 mmol), Sc(OTf)$_3$ (0.314 g, 0.637 mmol) and DMAP (0.389 g, 3.186 mmol) in CH$_2$Cl$_2$ (100 mL) was stirred for 0.5 h at −8° C. DIC (2.949 g, 23.37 mmol) was added dropwise, stirred for 0.5 h, warmed to r.t. slowly, filtered to recover the Lewis acid catalyst, the filtrate was quenched with diluted HCl and extracted with CH$_2$Cl$_2$. The combined organic phase was washed with NaHCO$_3$ aq, brine, dried over anhydrous Na$_2$SO$_4$. The solvent was removed under reduced pressure. Chromatography (silica gel, CH$_2$Cl$_2$/MeOH 30:1) gave the desired product as a mixture of diastereomer Fmoc-N-Me-D/L-Ala-MDC: white solid (0.8385 g, 90.5%). Further column chromatography (silica gel, CH$_2$Cl$_2$/MeOH 100:1 to 20:1) gave two fractions as pure diastereomer. The higher Rf fraction was determined to be the D-aminoacyl ester diastereomer (Fmoc-N-Me-D-Ala-MDC), while the lower Rf fraction was the desired L-aminoacyl ester (Fmoc-N-Me-L-Ala-MDC). Fmoc-N-Me-L-Ala-MDC: white solid (0.4262 g, 46.0% yield), $^1$H NMR (400 MHz, CDCl$_3$): δ 0.77 (3H, s), 1.22-1.32 (6H, m), 1.40-1.48 (1H, m), 1.63 (3H, s), 2.13 (1H, dd, J=14.4, 2.8 Hz), 2.53 (1H, dd, J=14.4, 10.8 Hz), 2.64 (3H, s), 2.88 (3H, s), 3.00 (1H, d, J=9.6 Hz), 3.07 (1H, d, J=12.4 Hz), 3.35 (3H, s), 3.48 (1H, d, J=8.8 Hz), 3.59 (1H, d, J=11.2 Hz), 3.97 (3H, s), 4.13-4.19 (1H, m), 4.15 (1H, s), 4.24 (1H, t, J=10.8 Hz), 4.72-4.77 (2H, m), 5.03 (1H, q, J=6.8 Hz), 5.65 (1H, dd, J=15.2, 9.2 Hz), 6.29 (1H, br), 6.41 (1H, dd, J=15.2, 11.2 Hz), 6.52 (1H, d, J=1.2 Hz), 6.70 (1H, d, J=10.8 Hz), 6.79 (1H, d, J=1.2 Hz), 7.33 (1H, t, J=7.6 Hz), 7.36 (1H, t, J=7.6 Hz), 7.39 (1H, d, J=7.6 Hz), 7.49 (1H, d, J=7.6 Hz), 7.70 (1H, d, J=7.6 Hz), 7.72 (1H, d, J=7.6 Hz). LC-MS (M+Na$^+$) calc.: 894.3. found: 894.3. Fmoc-N-Me-D-Ala-MDC: white solid (0.3993 g, 43.1% yield), $^1$H NMR (400 MHz, CDCl$_3$): δ 0.84 (3H, s), 1.22-1.27 (3H, m), 1.40-1.48 (1H, m), 1.51 (3H, d, J=7.6 Hz), 1.67 (3H, s), 2.20 (1H, dd, J=14.4, 2.8 Hz), 2.63 (1H, dd, J=14.4, 12.4 Hz), 2.85 (1H, d, J=9.6 Hz), 2.96 (3H, s), 3.17 (3H, s), 3.20 (1H, s), 3.24 (3H, s), 3.40 (1H, d, J=9.2 Hz), 3.51 (1H, d, J=12.8 Hz), 3.99 (3H, s), 4.20-4.28 (2H, m), 4.38-4.43 (2H, m), 4.80-4.98 (2H, m), 5.80 (1H, dd, J=15.2, 11.2 Hz), 6.18 (1H, s), 6.25 (1H, d, J=10.8 Hz), 6.40 (1H, dd, J=15.2, 11.2 Hz), 6.79 (1H, d, J=1.6 Hz), 6.84 (1H, d, J=1.6 Hz), 7.32 (2H, t, J=7.6 Hz), 7.41 (2H, t, J=7.6 Hz), 7.61 (2H, d, J=7.6 Hz), 7.77 (2H, d, J=7.6 Hz). LC-MS (M+Na$^+$) calc.: 894.3. found: 894.3.

Example 2

Deprotection of Fmoc-N-Me-D/L-Ala-MDC (N-Me-D/L-Ala-MDC)

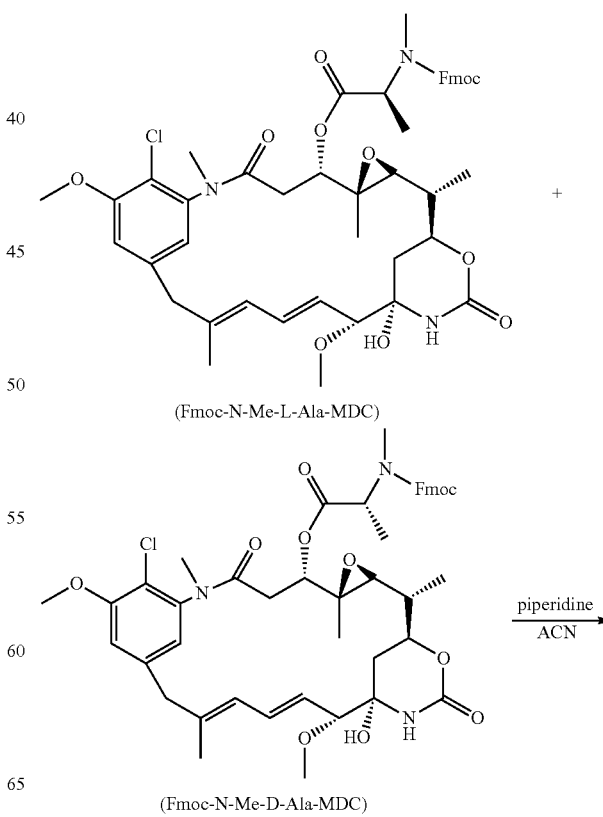

(Fmoc-N-Me-L-Ala-MDC)

(Fmoc-N-Me-D-Ala-MDC)

piperidine / ACN →

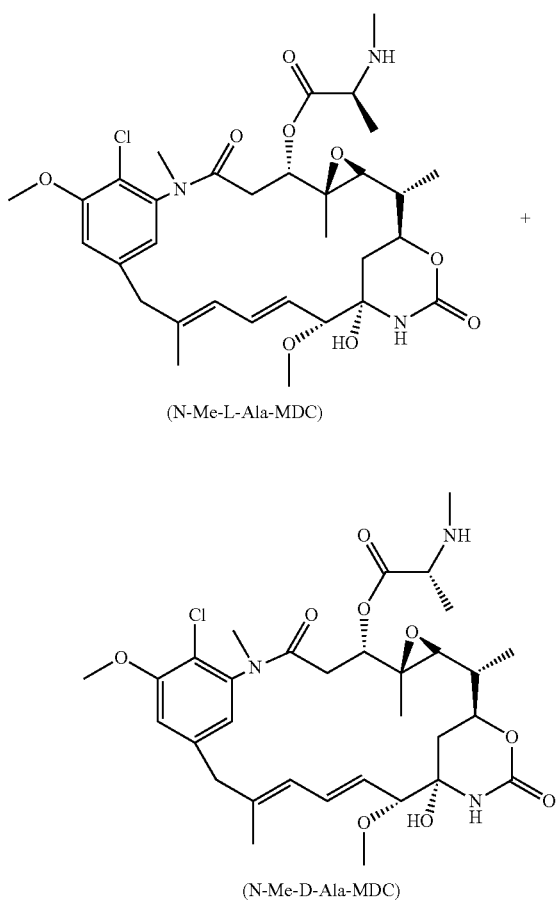

(N-Me-L-Ala-MDC)

(N-Me-D-Ala-MDC)

Into Fmoc-N-Me-D/L-Ala-MDC (0.463 g, 0.5307 mmol) in ACN (200 mL) was added piperidine (0.865 g, 10.15 mmol). The mixture was stirred at r.t. for 4 h, quenched with water and extracted with CH$_2$Cl$_2$. The combined organic phase was washed with brine and dried over Na$_2$SO$_4$. The solvent was removed under reduced pressure to give the crude product, which was used in the next step without further purification. LC-MS (M+H$^+$) calc.: 650.3. found: 650.3. Rt: 3.96 min.

Example 3

Deprotection of Fmoc-N-Me-L-Ala-MDC (N-Me-L-Ala-MDC)

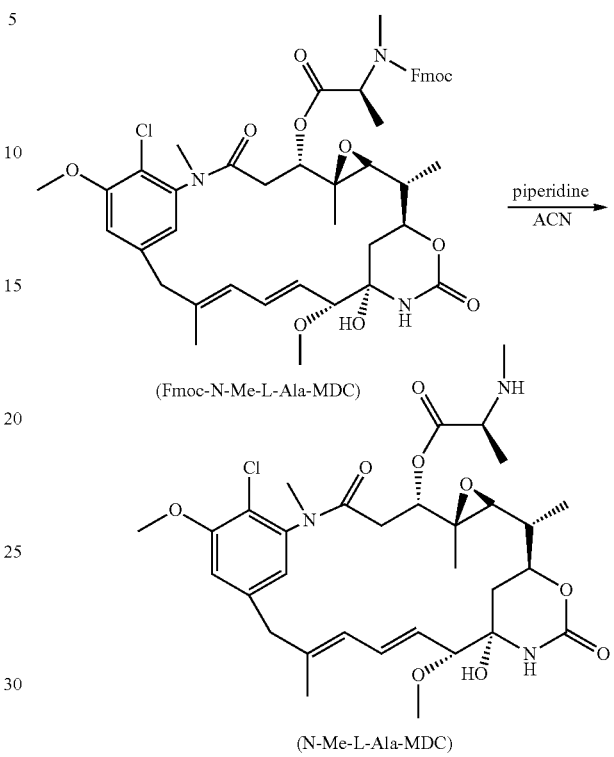

(Fmoc-N-Me-L-Ala-MDC)

(N-Me-L-Ala-MDC)

Into Fmoc-N-Me-L-Ala-MDC (0.463 g, 0.5307 mmol) in ACN (200 mL) was added piperidine (0.865 g, 10.15 mmol). The mixture was stirred at r.t. for 4 h, quenched with water and extracted with CH$_2$Cl$_2$. The combined organic phase was washed with brine and dried over Na$_2$SO$_4$. The solvent was removed under reduced pressure to give the crude product, which was used in the next step without further purification. LC-MS (M+H$^+$) calc.: 650.3. found: 650.3. Rt: 3.96 min.

Example 4

Condensation of N-Me-D/L-Ala-MDC with MA-ACP (D-3AA-MDC and L-3AA-MDC)

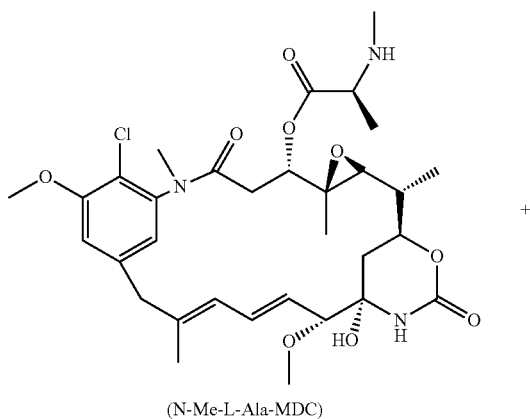

(N-Me-L-Ala-MDC)

+

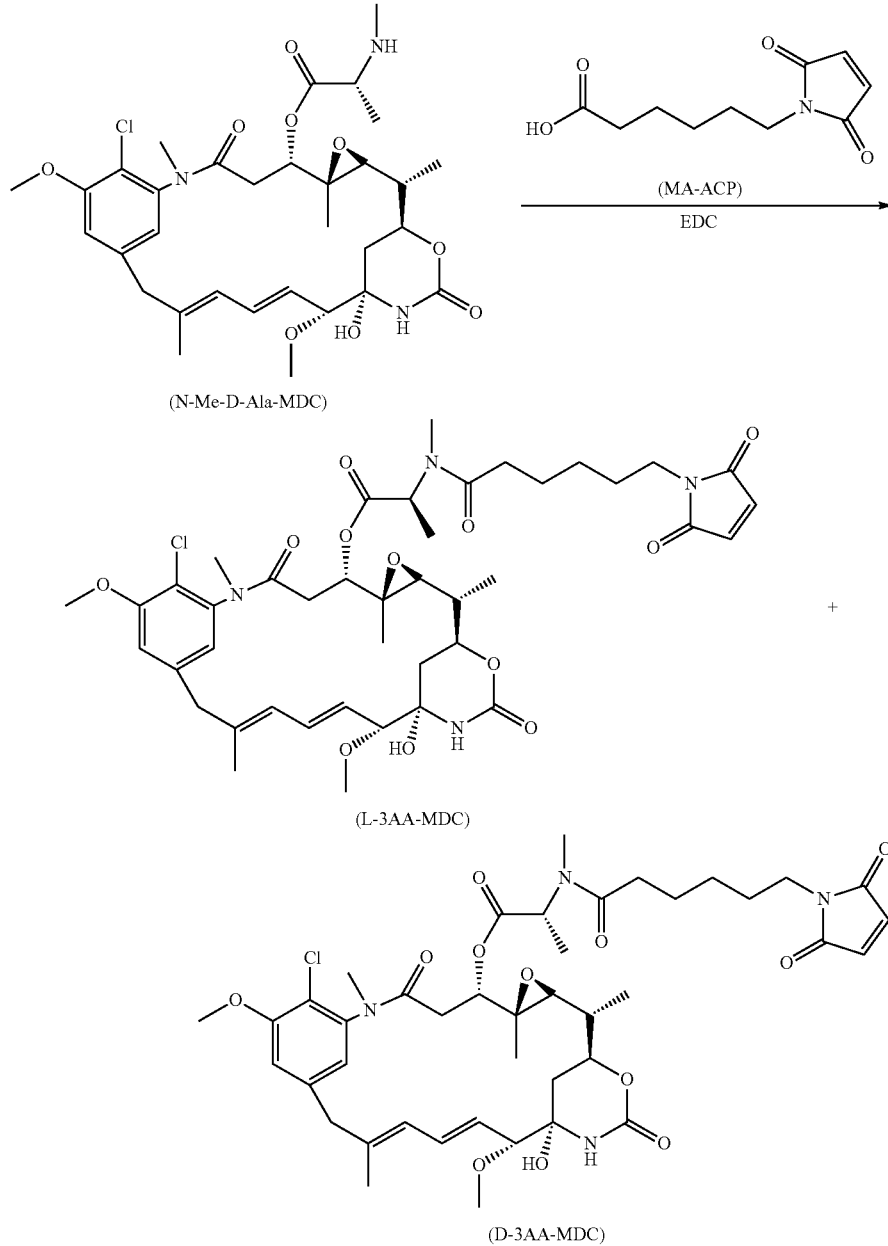

Into above prepared N-Me-D/L-Ala-MDC (0.5307 mmol) and MA-ACP (0.448 g, 2.123 mmol) in DMF (25 mL) under 0° C. was added EDC (0.407 g, 2.123 mmol). The mixture was stirred at r.t. overnight, quenched with water, extracted with EtOAc, washed with brine, and dried over Na$_2$SO$_4$. The solvent was removed under reduced pressure. Chromatography (silica gel: CH$_2$Cl$_2$/MeOH 30:1) gave the crude product. Further purification by preparative HPLC on a YMC C-18 column (250×20 mm, S 10 μm) gave two fractions (Rt=6.59 min and 6.98 min) as white solid. The higher Rt fraction was determined to be the D-aminoacyl ester diastereomer (D-3AA-MDC, 45.2%), while the lower Rt fraction was the desired L-aminoacyl ester (L-3AA-MDC, 54.8%). L-3AA-MDC: white solid (0.1364 g, 30.5% overall yield over two steps), $^1$H NMR (400 MHz, CDCl$_3$): δ 0.79 (3H, s), 1.17-1.32 (3H, m), 1.27 (3H, s), 1.29 (3H, s), 1.40-1.76 (7H, m), 2.12-2.23 (2H, m), 2.31-2.45 (1H, m), 2.59 (1H, t, J=12.8 Hz), 2.82 (3H, s), 3.01 (1H, d, J=9.6 Hz), 3.10 (1H, d, J=8.8 Hz), 3.17 (3H, s), 3.34 (3H, s), 3.42 (2H, t, J=6.8 Hz), 3.48 (2H, d, J=6.8 Hz), 3.62 (1H, d, J=12.8 Hz), 3.97 (3H, s), 4.27 (1H, t, J=11.2 Hz), 4.76 (1H, d, J=11.6 Hz), 5.36 (1H, q, J=6.8 Hz), 5.65 (1H, dd, J=15.2, 9.2 Hz), 6.25 (1H, s), 6.41 (1H, dd, J=15.2, 11.2 Hz), 6.64 (1H, s), 6.65 (2H, s), 6.72 (1H, d, J=11.2 Hz), 6.82 (1H, s). LC-MS (M+Na$^+$) calc.: 865.3. found: 865.3. Rt: 6.59 min. D-3AA-MDC: white solid (0.1128 g, 25.2% overall yield over two steps), $^1$H NMR (400 MHz, CDCl$_3$): δ 0.86 (3H, s), 1.22-1.38 (4H, m), 1.25 (3H, d, J=9.2 Hz), 1.38-1.45 (1H, m), 1.48 (3H, d, J=7.6 Hz), 1.56-1.70 (4H, m), 1.68 (3H, s), 1.75 (1H, d, J=13.6 Hz), 2.19 (1H, dd, J=14.4, 2.8 Hz), 2.28-2.36 (2H, m), 2.65 (1H, dd, J=14.2, 12.0 Hz), 2.80 (1H, d, J=9.6 Hz), 3.01 (3H, s), 3.19 (1H, d, J=13.2 Hz), 3.32 (3H, s), 3.42

(1H, d, J=9.6 Hz), 3.47-3.54 (3H, m), 3.98 (3H, s), 4.29 (1H, t, J=10.4 Hz), 4.88 (1H, dd, J=11.8, 3.2 Hz), 5.07 (1H, q, J=7.6 Hz), 5.84 (1H, dd, J=15.2, 9.2 Hz), 6.23 (1H, d, J=11.2 Hz), 6.27 (1H, s), 6.41 (1H, dd, J=15.2, 11.2 Hz), 6.69 (2H, s), 6.79 (1H, d, J=1.2 Hz), 6.84 (1H, d, J=1.2 Hz). LC-MS (M+Na$^+$) calc.: 865.3. found: 865.3. Rt: 6.98 min.

Example 5

Condensation of N-Me-L-Ala-MDC with MA-ACP (L-3AA-MDC)

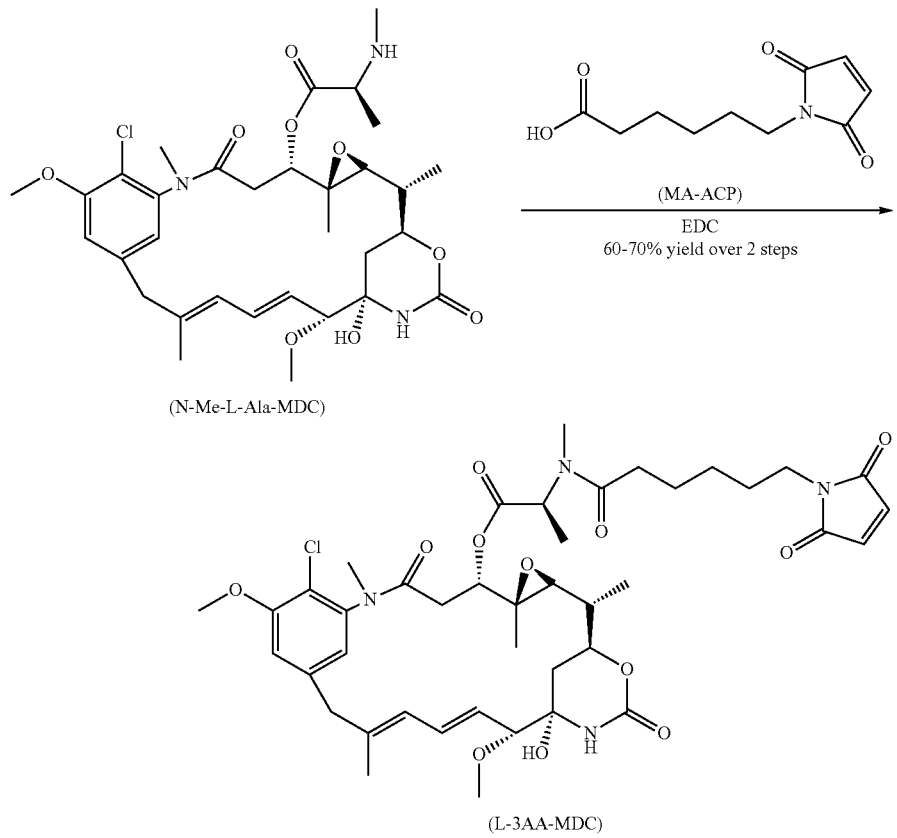

Into above prepared N-Me-L-Ala-MDC (0.5307 mmol) and MA-ACP (0.448 g, 2.123 mmol) in DMF (25 mL) under 0° C. was added EDC (0.407 g, 2.123 mmol). The mixture was stirred at r.t. overnight, quenched with water, extracted with EtOAc, washed with brine, dried over Na$_2$SO$_4$. The solvent was removed under reduced pressure. Chromatography (silica gel: CH$_2$Cl$_2$/MeOH 30:1) gave the crude product. Further purification by preparative HPLC on a YMC C-18 column (250×20 mm, S 10 μm) gave the desired L-3AA-MDC: white solid (0.280 g, 62.6% overall yield over two steps), $^1$H NMR (400 MHz, CDCl$_3$): δ 0.79 (3H, s), 1.17-1.32 (3H, m), 1.27 (3H, s), 1.29 (3H, s), 1.40-1.76 (7H, m), 2.12-2.23 (2H, m), 2.31-2.45 (1H, m), 2.59 (1H, t, J=12.8 Hz), 2.82 (3H, s), 3.01 (1H, d, J=9.6 Hz), 3.10 (1H, d, J=8.8 Hz), 3.17 (3H, s), 3.34 (3H, s), 3.42 (2H, t, J=6.8 Hz), 3.48 (2H, d, J=6.8 Hz), 3.62 (1H, d, J=12.8 Hz), 3.97 (3H, s), 4.27 (1H, t, J=11.2 Hz), 4.76 (1H, d, J=11.6 Hz), 5.36 (1H, q, J=6.8 Hz), 5.65 (1H, dd, J=15.2, 9.2 Hz), 6.25 (1H, s), 6.41 (1H, dd, J=15.2, 11.2 Hz), 6.64 (1H, s), 6.65 (2H, s), 6.72 (1H, d, J=11.2 Hz), 6.82 (1H, s). LC-MS (M+Na$^+$) calc.: 865.3. found: 865.3. Rt: 6.59 min.

Example 6

Figure 6:
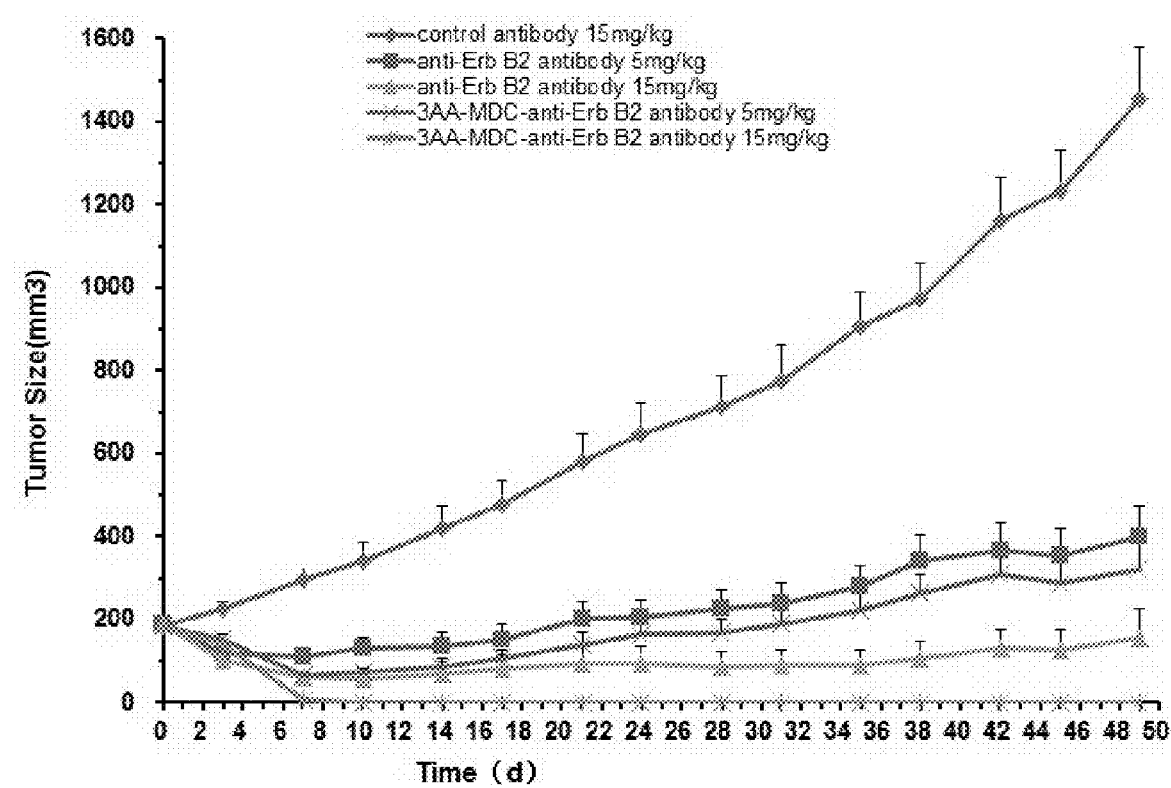
FIG. 6 shows that 3AA-MDC-anti-HER2 (Erb B2/NEU) antibody eradicated human BT474 tumor in mouse xenografts.

The Effect of the Metabolites of Prodrug Antibody Maytansinoid Conjugates on the Tubulin Polymerization The effect of 3AA-MDC, 206-3AA-MDC and the metabolites (Cys-3AA-MDC and Lys-mcc-MDC) of prodrug antibody maytansinoid conjugates on the tubulin polymerization in vitro was assessed by HTS-Tubulin Polymerization Assay Kit (BK004P, Cytoskeleton, Inc., USA). According to the instruction of kit, pre-warm the 96-well plate to 37° C. for 30 min prior to starting the assay. At the same time, the spectrophotometer (SpectraMax, Molecular Devices, USA) was set as follow: wavelength, 405 nm; temperature, 37° C.; Kinetic, 31 cycles of 1 reading per minute. Make cold G-PEM buffer (990 μL General Tubulin Buffer+10 μL GTP Stock) and keep it on ice. Prepare 4 mg/mL tubulin, 1 μM L-3AA-MDC (N$_2$'-deacetyl-N$_2$'-(6-maleimido-1-oxo-hexyl)maytansine), 1 μM 206-3AA-MDC, 1 μM cys-3AA-MDC, 1 μM lys-mcc-MDC, 100 μM Paclitaxel, and 100 μM Nocodazole. Add 10 μL G-PEM, 3AA-MDC, 206-3AA-MDC, cys-3AA-MDC, lys-mcc-MDC, Paclitaxel, Nocodazole into the wells, and then add 100 μL 4 mg/ml tubulin to each well. Immediately place the plate into the spectrophotometer and start recording using the kinetic setup described above. As show in the FIG. 6, compared with the PBS buffer, 3AA-MDC, Cys-3AA- MDC, Lys-mcc-MDC and 206-3AA-MDC more significantly inhibited the tubulin polymerization (FIG. 6). Nocodazole, the tubulin polymerization inhibitor, was set as a negative control. The metabolite Cys-3AA-MDC was prepared by reaction of 3AA-MDC with cysteine under the base DIEA in $CH_2Cl_2$. LC-MS (M+H$^+$) calc.: 964.5. found: 964.2. Rt: 12.97 min. The metabolite Lys-MCC-MDC was prepared by reaction of SMCC-MDC with lysine under the base DIEA in DMF. LC-MS (M+H$^+$) calc.: 1103.7. found: 1103.2. Rt: 13.00 and 13.18 min.

Example 7

The Effect of 3AA-MDC and Related Metabolites on the Tubulin Polymerization

The effect of 3AA-MDC and related metabolites on the tubulin polymerization in vitro was assessed by HTS-Tubulin Polymerization Assay Kit (BK004P, Cytoskeleton, Inc., USA). According to the instruction of kit, pre-warm the 96-well plate to 37° C. for 30 min prior to starting the assay. At the same time, the spectrophotometer (SpectraMax, Molecular Devices, USA) was set as follow: wavelength, 405 nm; temperature, 37° C.; Kinetic, 31 cycles of 1 reading per minute. Make cold G-PEM buffer (990 μL General Tubulin Buffer+10 μL GTP Stock) and keep it on ice. Prepare 4 mg/ml tubulin, 200 nM L-3AA-MDC (N2'-deacetyl-N2'-(6-maleimido-1-oxo-hexyl)maytansine), or related compounds cys-3AA-MDC, or lys-mcc-MDC, 100 μM Paclitaxel, 100 μM Nocodazole, and 1 μM 206-3AA-MDC (3AA-MDC-antibody). Add 10 μL G-PEM, 3AA-MDC, Paclitaxel, Nocodazole and 206-3AA-MDC or related metabolites into the wells, and then add 100 μL 4 mg/ml tubulin to each well. Immediately place the plate into the spectrophotometer and start recording using the kinetic setup described above. As show in the FIG. 1, the relative activity of tubulin polymerization was enhanced about 3 fold in the presence of Paclitaxel and decreased 2.5 fold in the presence of Nocodazole. L-3AA-MDC and other related metabolites more significantly inhibited the tubulin polymerization (FIG. 1).

Example 8

Recombinant Antibody Expression and Purification

The anti-ERB B2/NEU antibody was produced in CHO cells essentially as described in Wood et al., J Immunol. 145:3011 (1990). Briefly, each of the antibody genes were constructed with molecular biology techniques (Molecular Cloning: A Laboratory Manual, 3$^{rd}$ edition J. Sambrook et al., Cold spring Harbor Laboratory Press). A derivative of Chinese hamster ovary cell lines CHOK1 was grown in CD-CHO media (GIBCO). Transfections were facilitated using electroporation. Healthy mid-log CHO-K1 cells were pelleted by centrifuge and were resuspended in fresh CD-CHO media to achieve cell densities of approximately $1×10^7$ cells (600 mL) per cuvette. Suspensions of cells containing 40 μg of linearized plasmid DNA were electroporated, seeding $10^3$ cells per well in 96-well tissue culture plates containing suitable selection drug. The antibody expression level in the culture supernatant of clones isolated on 96-well tissue culture plates was determined by an enzyme-linked immunosorbent assay (ELISA). On the basis of the antibody titer in the supernatant, clones with high-level expression were transferred to 24-well plate (Corning) containing suitable media. Specific antibody productivity (qAb) and specific growth rate (μ) were further analyzed by seeding cells at $2×10^5$ cells per well containing 5 mL of medium in six-well tissue culture plates, culturing for 2 and 4 days, and usually 20-30 high-producing clones (parental clones) were transferred to shake flask for successive selection, and 5-8 highest producer clones were chosen to be further subcloned, and tested for expression.

The purification was carried out by centrifuging cell suspension and harvesting the supernatant, which was further cleared by centrifuging. Protein A affinity columns such as Mab Select SuRe (GE Healthcare) and ion exchange such as Capto S (GE) were used to purify the expressed antibodies).

Example 9

Conjugation of Anti-Erb B2/neu Antibody with SMCC-MDC

The drug-linker SMCC-MDC was prepared in the following reactions: (1) 3-mercaptopropanoic acid (MPr) was reacted with N-succinimidyl 4-(maleimidomethyl) cyclohexane-1-carboxylate (SMCC) in the presence of N,N-diisopropylethylamine (DIEA), giving the MPr-SMCC at a yield of over 95%; (2) condensation of N-Me-L-Ala-MDC, which was prepared by deprotection of Fmoc-N-Me-Ala-MDC under a base piperidine in $CH_3CN$, with MPr-SMCC under a coupling reagent EDC, giving the desired coupled product SMCC-MDC in 60-70% yield over two steps. Anti-Erb B2/neu antibody was diluted to 2.5 mg/mL in solution A (50 mM potassium phosphate, 50 mM NaCl, and 2 mM EDTA, pH 6.5). SMCC-MDC was added to give a ratio of SMCC-MDC to antibody of 7:1 mole equivalent. Then DMA (dimethylacetamide) was added to 15% (v/v) to the reaction and reaction was mixed by stirring for 4 h at ambient temperature. D-Lmcc-Anti-Erb B2/neu antibody conjugate was purified from excess unreacted or hydrolyzed reagent and excess SMCC-MDC using a G25 gel filtration column equilibrated in pH 7.4 phosphate buffer (aqueous). The conjugate was then dialyzed overnight into pH 7.4 phosphate buffer (aqueous) and then filtered through a 0.22 ☐m filter for final storage. The number of SMCC-MDC molecule per antibody molecule in the final conjugate was measured by determining absorbance of the conjugate at 252 and 280 nm and using known extinction coefficients for SMCC-MDC and antibody at these two wavelengths. A ratio of maytansinoid compound to antibody of 3.5:1.0 was normally obtained.

Example 10

Conjugation of Anti-Erb B2/neu Antibody with Derivatized Maytansinoid

Anti-Erb B2/neu antibody was diluted to 8.0 mg/mL in solution B (50 mM potassium phosphate, 50 mM NaCl, and 2 mM EDTA, pH 8.0). Partial reduction was carried out with (6 moles equivalent) DTT. After incubation at 37° C. for 60 minutes, the buffer was exchanged by elution through Sephadex G-25 resin with solution B. The thiol-antibody value was determined from the reduced monoclonal antibody (mAb) concentration determined from 280-nm absorbance, and the thiol concentration was determined by reaction with DTNB (5,5'-dithiobis(2-nitrobenzoic acid); Aldrich) and absorbance measured at 412 nm.

The conjugation reaction was carried out with 10% DMA (dimethylacetamide). The volume of 3AA-MDC (the linked drug N2'-deacetyl-N2'-(6-maleimido-1-oxo-hexyl) maytansine) solution was calculated to contain 1.5-mol 3AA-MDC per mol thiol equivalent. 3AA-MDC solution was added rapidly with mixing to the cold-reduced antibody solution, and the mixture was stirred at r.t. for 3 hours, and continued for additional 1 h after adding 5 mM cysteine. The reaction mixture was concentrated by centrifugal ultrafiltration and buffer-exchanged by elution through Sephadex G25 equilibrated in PBS. The conjugate was then filtered through a 0.2-μm filter under sterile conditions and stored at −80° C. for analysis and testing. The 3AA-MDC-antibody was further analyzed for drug/antibody ratio by measuring unreacted thiols with DTNB, and 3.5:1 ratio of drug/antibody was often obtained. 3AA-MDC-antibody was further characterized for concentration by UV absorbance, aggregation by size-exclusion chromatography, and residual free drug by reverse-phase HPLC. All mAbs and ADCs used in these studies exceeded 98% monomeric protein.

Example 11

Preparation of Conjugated D-LSPP-Anti-Erb B2/neu Antibody

Anti-Erb B2/neu antibody (8 mg/mL) was modified using 8-fold molar excess of N-succinimidyl-4-(2-pyridyldithio)pentanoate (SPP) to introduce dithiopyridyl groups. The reaction was carried out in 95% v/v Buffer A (50 mM potassium phosphate, 50 mM NaCl, 2 mM EDTA, pH 6.5) and 5% v/v dimethylacetamide (DMA) for 2 h at room temperature. The slightly turgid reaction mixture was gel-filtered through a Sephadex G25 column (equilibrated in Buffer A). The degree of modification was determined by measuring the absorbance of the antibody and the 2-mercaptopyridine (Spy) released by DTT respectively at 280 and 343 nm. Modified anti-Erb B2/neu antibody was then conjugated at 2.5 mg/mL using a 1.7-fold molar excess of NT-deacetyl-N-2'(3-mercapto-1-oxopropyl)-maytansine over SPy. The reaction was carried out with DMA (5% v/v) in Buffer A (see above). The reaction was incubated at room temperature overnight for 17 h. The conjugated antibody was cleared by centrifugation and then further purified through gel-filtration with a Sephadex G25 column equilibrated with PBS pH 6.5. The conjugate was sterile-filtered using a 0.22 μM Millex-GV filter. The number of drug molecules linked per anti-Erb B2/neu antibody molecule was determined by measuring the absorbance at both 252 nm and 280 nm of the filtered material. The drug to antibody ratio was found to be about 4.5. The conjugated antibody was further biochemically characterized by size exclusion chromography (SEC) and found to be over 96% monomer.

Example 12

The stability studies of 3AA-MDC-anti-Erb B/neu antibody were evaluated in Sprague-Dawley rats. Sprague-Dawley rats were administered 10 mg/kg 3AA-MDC-anti-Erb B/neu (based on the antibody component) by tail vein injection. Blood samples were collected from each mouse via the saphenous vein at 0 h, 10 min, 30 min, 1 h, 2 h, 4 h, 8 h, 24 h, 36 h, day 2, day 3, day 4, day 7, day 14, day 21, day 28 after injection. Blood was collected into heparin coated tubes followed by centrifugation (14,000×g, 3 minutes) to isolate plasma. Plasma concentrations of total Anti-Erb B/neu and antibody-drug conjugates were measured by ELISA. Total antibody concentration in the serum samples was measured as follows: 96-well ELISA plates were coated with HER2 ECD in 2 μg/mL carbonate/bicarbonate buffer (pH 9.6) at 4° C. overnight. After removal of the coat solution, nonspecific binding sites were blocked by incubating with blocking solution (PBS, 1% BSA, 0.05% Tween 20) at room temperature for 1 hour. The plates were then washed with wash buffer (0.05% Tween in PBS), and standards or samples diluted in PBS were added. After a 2 h incubation, plates were washed and mouse anti-human IgG-horseradish peroxidase conjugate (Sigma, St. Louis, Mo.) was added for an additional 2 h. Plates were then washed again. Subsequently, 100 μL of 3,3,5,5-tetramethylbenzidine (Sigma, St. Louis, Mo.) were added to each well, and upon color development, the reaction was stopped with 100 μL of 1 N sulfuric acid. Absorbance was measured using a VMax Kinetic Microplate reader (Molecular Devices, Sunnyvale, Calif.) at 490 nm. For measurement of antibody-drug conjugates concentration, wells were coated with HER2 ECD and serum samples added as above. After the 2-h sample incubation, the plates were washed, rabbit anti-maytansine antibody was added to each well, and the plates were incubated for 1 h. Plates were then washed, and HRP-conjugated goat anti-rabbit IgG (Sigma) was added for an additional 1 h incubation. Color detection and measurement were performed as described above. Noncompartmental pharmacokinetic parameters were calculated with WinNonlin (Pharsight, Mountain View, Calif.). The time-concentration curves of antibody component of 3AA-MDC-antibody and the drug component of 3AA-MDC-antibody appeared to follow bi-exponential declines. The terminal half-life of antibody component of 3AA-MDC-antibody was 571.07, and the terminal half-life of drug component of 3AA-MDC-antibody was 88.36 hours.

Example 13

Figure 2:
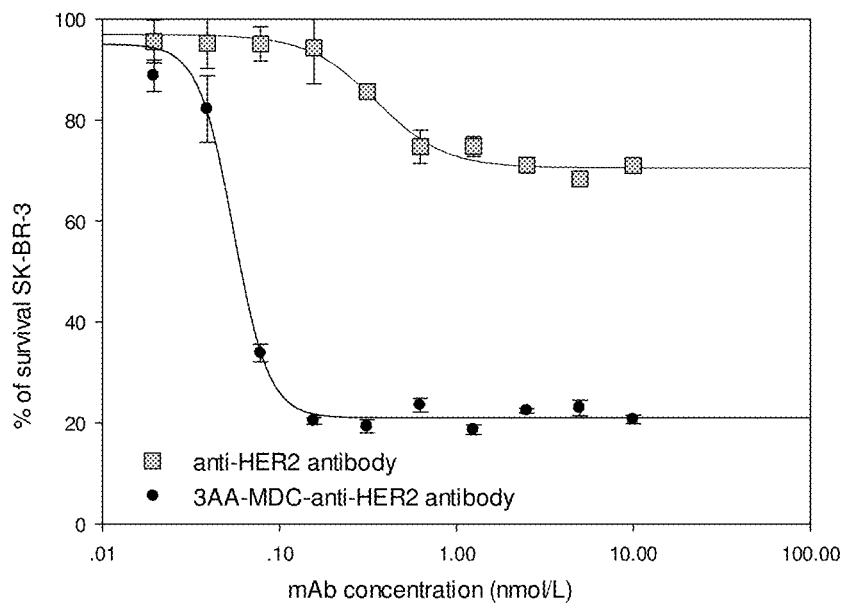
FIG. 2 shows anti-Erb B2/neu antibody and 3AA-MDC-antibody inhibited tumor cell SK-BR-3 growth.
Figure 3:
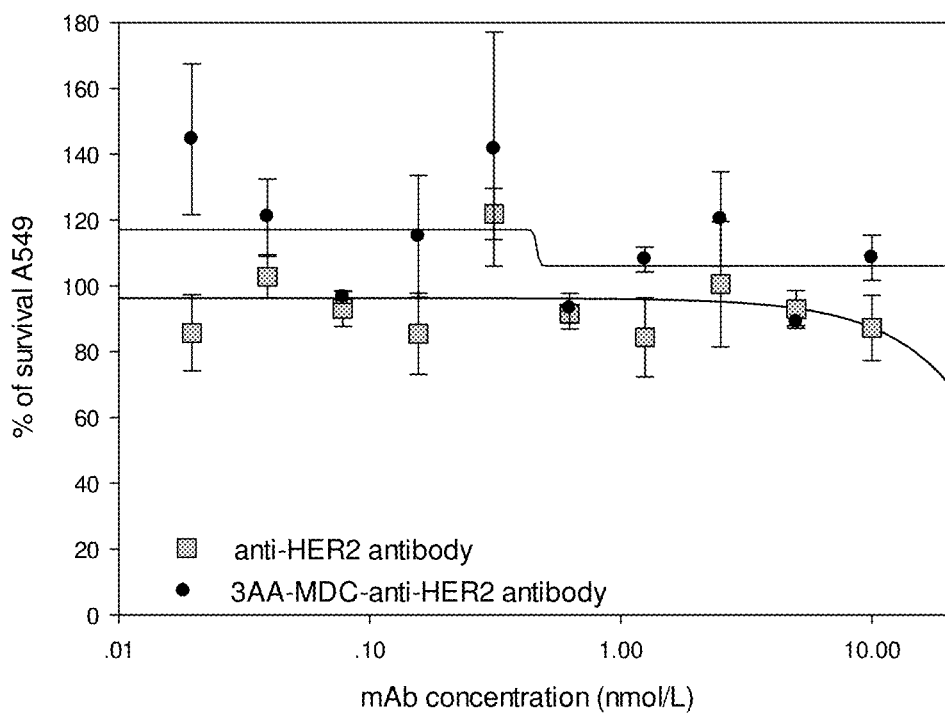
FIG. 3 shows Anti-Erb B2/NEU antibody or 3AA-MDC-Anti-ERB B2/NEU antibody has no inhibitory effect on Erb B2/NEU negative A549 negative cells.

Characterization of Anti-ErbB2 Antibody Drug Conjugate 3AA-MDC-Anti-Erb B2 Antibody The growth inhibitory characteristics of Anti-Erb B2 antibody and 3AA-MDC-anti-Erb B2 antibody were evaluated using the Her2 positive breast tumor cell line, SK-BR-3 (see Hudziak et al. Molec. Cell. Biol. 9 (3):1165 1172 (1989)) and Her2 negative cell line A549 [Shanghai Cell Collections, ltd., Co., Shanghai, China]. Briefly, cells were detached by using 0.25% (vol/vol) trypsin and suspended in complete medium. Aliquots of 100 □L containing 10,000 cells for SK-BR-3 cell line and 8,000 cells for A549 cell line were plated into 96-well microdilution plates. The cells were allowed to adhere overnight at 37° C., and 100 □L of media containing various concentrations of anti-Erb B2 antibody and 3AA-MDC-anti-Erb B2 antibody was then added. After 72 hours, plates were washed twice with PBS (pH 7.5), and analyzed for relative cell proliferation with CCK-8 reagent (Cell Counting kit-8, Dojindo, Japan). Drug conjugate 3AA-MDC-anti-Erb B2 antibody more significantly inhibited the Her2 positive cell proliferation than naked anti-Erb B2 antibody (FIG. 2). Neither naked antibody anti-Erb B2 antibody nor drug conjugate 3AA-MDC-anti-Erb B2 antibody inhibited the growth of Her2 negative cell line A549 (FIG. 3).

Example 14

Figure 4:
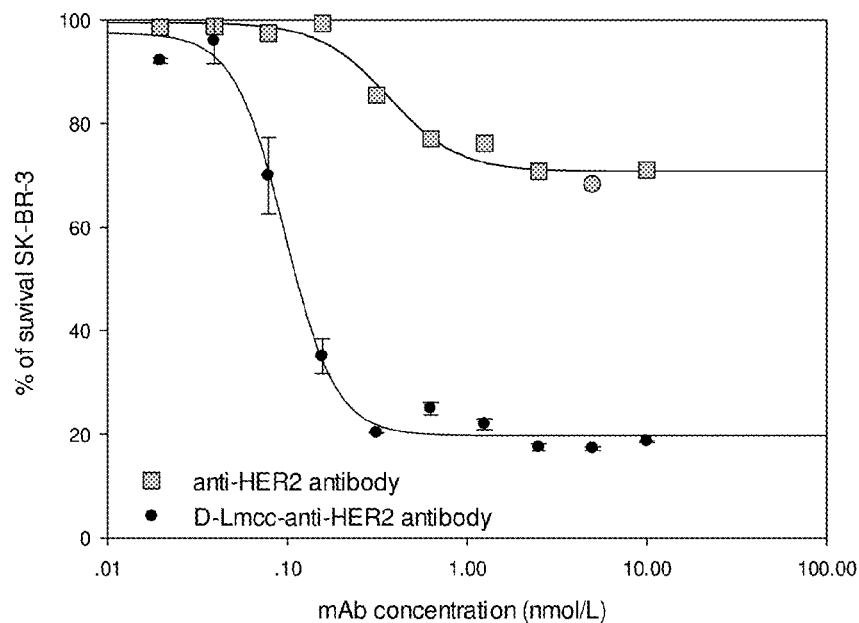
FIG. 4 shows the inhibitory effect of D-Lmcc-Anti-Erb B2/neu antibody towards SK-BR-3 cells.
Figure 5:
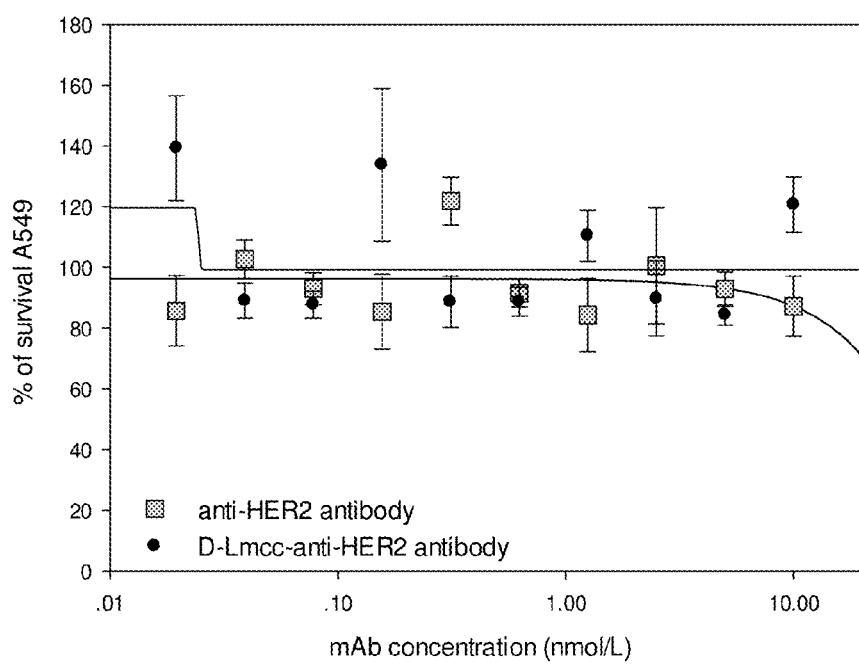
FIG. 5 shows that Anti-Erb B2/NEU antibody or D-Lmcc-Anti-Erb B2/neu antibody has no inhibitory effect on ERB B2/NEU negative A549 cells.

Characterization of Anti-ErbB2 Antibody Drug Conjugate D-Lmcc-Anti-Erb B2 Antibody The growth inhibitory characteristics of D-Lmcc-anti-Erb B2 antibody were evaluated using the Her2 positive breast tumor cell line, SK-BR-3 (see Hudziak et al. Molec. Cell. Biol. 9 (3):1165 1172 (1989) and Her2 negative cell line A549. Briefly, cells were detached by using 0.25% (vol/vol) trypsin and suspended in complete medium. Aliquots of 100 □L containing 10,000 cells for SK-BR-3 cell line and 8,000 cells for A549 cell line were plated into 96-well microdilution plates. The cells were allowed to adhere overnight at 37° C., and 100 □L of media containing various concentrations of anti-Erb B2 antibody and D-Lmcc-anti-Erb B2 antibody was then added. After 72 hours, plates were washed twice with PBS (pH 7.5), and analyzed for relative cell proliferation with CCK-8 reagent. Drug conjugate D-Lmcc-anti-Erb B2 antibody strongly inhibited the Her2 positive cell proliferation (FIG. 4). Neither naked antibody anti-Erb B2 antibody nor drug conjugate D-Lmcc-anti-Erb B2 antibody inhibited the growth of her2 negative cell line A549 (FIG. 5).

Example 15

3AA-MDC-anti-Erb B2 Antibody Eradicates Human BT474 Tumor Xenografts

In Vivo Tumor Studies: The effects of 3AA-MDC-anti-Erb B2 antibody on the growth of established tumors were examined on human BT474 tumor xenografts. Human BT474 cells (ATCC, HTB-20) were cultured in DMEM medium supplemented with 10% fetal bovine serum, 2 mM glutamine and antibiotics. Female BALB/c nude mice, 8-9 weeks old, were injected subcutaneously with $1 \times 10^7$ tumor cells in the dorsal area in a volume of 100 μL. When the tumor xenografts reaches a size of 150-200 mm$^3$ (calculated as 0.5×(length×width$^2$), animals were then treated with anti-Erb B2 antibody (5 or 15 mg/kg), 3AA-MDC-anti-Erb B2 antibody (5 or 15 mg/kg), or control antibody (Rituximab, 15 mg/kg). Animals were dosed every 3 weeks for a total of 3 doses i.v. in a volume of 100 μL. Each group consisted of 10 mice. Tumor size was determined at 3 days intervals. 49 days after tumor cell inoculation, animals were euthanized and tumors were removed and weighed. As shown in FIG. 6, Rapid tumor shrinkage was seen by 3AA-MDC-anti-Erb B2 antibody (15 mg/kg) from day 7. From day 10 onwards 3AA-MDC-anti-Erb B2 antibody (15 mg/kg) treated tumors had shrunken to non-palpable. Compared to the unconjugated Anti-Erb B2 antibody, 3AA-MDC-anti-Erb B2 antibody more significantly inhibited the tumor growth as assessed by tumor weight measurements 49 days after drug treatment.

Example 16

3AA-MDC-Anti-Erb B2 Antibody Eradicates Human NCI-N87 Tumor Xenografts

Figure 7:
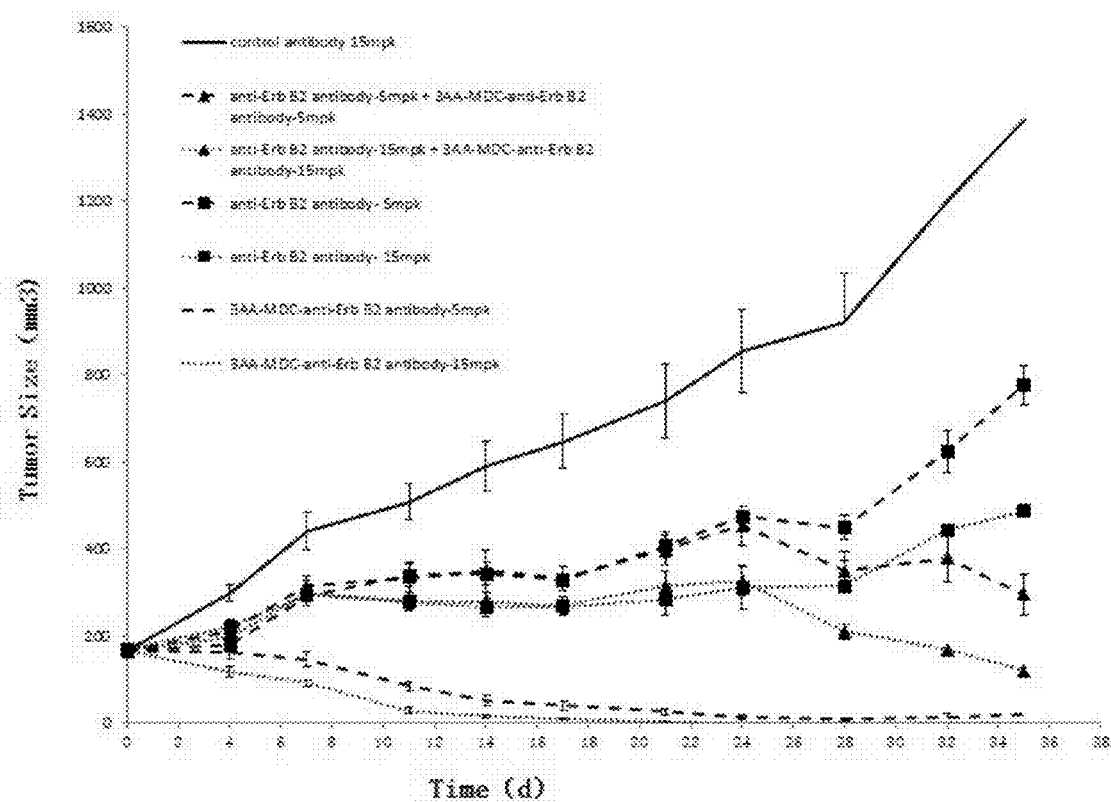
FIG. 7 shows that 3AA-MDC-anti-HER2 (Erb B2/NEU) antibody eradicated human NCI-N87 tumor in mouse xenografts.

In Vivo Tumor Studies: The effects of 3AA-MDC-anti-Erb B2 antibody on the growth of established tumors were examined on human NCI-N87 tumor xenografts. Human NCI-N87 cells (ATCC, CRL-5822) were cultured in DMEM medium supplemented with 10% fetal bovine serum, 2 mM glutamine and antibiotics. Female BALB/c nude mice, 4-8 weeks old, were injected subcutaneously with $5 \times 10^6$ tumor cells in the dorsal area in a volume of 100 μL. When the tumor xenografts reaches a size of 100-200 mm$^3$ (calculated as 0.5×(length×width$^2$)), animals were then treated with Anti-Erb B2 antibody (5 or 15 mg/kg, i.v), 3AA-MDC-anti-Erb B2 antibody (5 or 15 mg/kg, i.v), or control antibody (Rituximab, 15 mg/kg, i.v). Animals were dosed once per week for a total of 5 doses i.v. in a volume of 100 μL. Anti-Erb B2 antibody treatment of NCI-N87 xenografts was discontinued on day 15 and switched to 3AA-MDC-anti-Erb B2 antibody (5 or 15 mg/kg, i.v.) from the day 21 onwards. Each group consisted of 10 mice. Tumor size was determined at 3 days intervals. 42 days after tumor cell inoculation, animals were euthanized and tumors were removed and weighed. As shown in FIG. 7, rapid tumor shrinkage was seen by 3AA-MDC-anti-Erb B2 antibody (5 or 15 mg/kg) from day 11. From day 32 onwards 3AA-MDC-anti-Erb B2 antibody (5 or 15 mg/kg) treated tumors had shrunken to non-palpable. Compared to the unconjugated anti-Erb B2 antibody, at 5 or 15 mg/kg dose tested, 3AA-MDC-anti-Erb B2 antibody more significantly inhibited the tumor growth as assessed by tumor weight measurements 42 days after drug treatment.

Example 17

Cellular Metabolites of 3AAMDC-Antibody and D-Lmcc-Anti-Erb B2 Antibody

Figure 8:
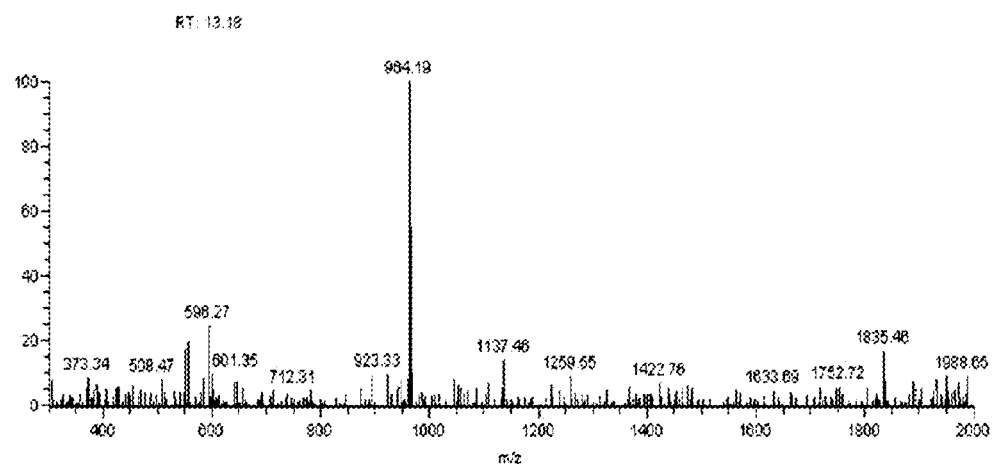
FIG. 8 shows a mass spectrum of 3AA-MDC, which was the metabolites of a prodrug the anti-Her2 antibody Cysteine-3AA-MDC
Figure 9:
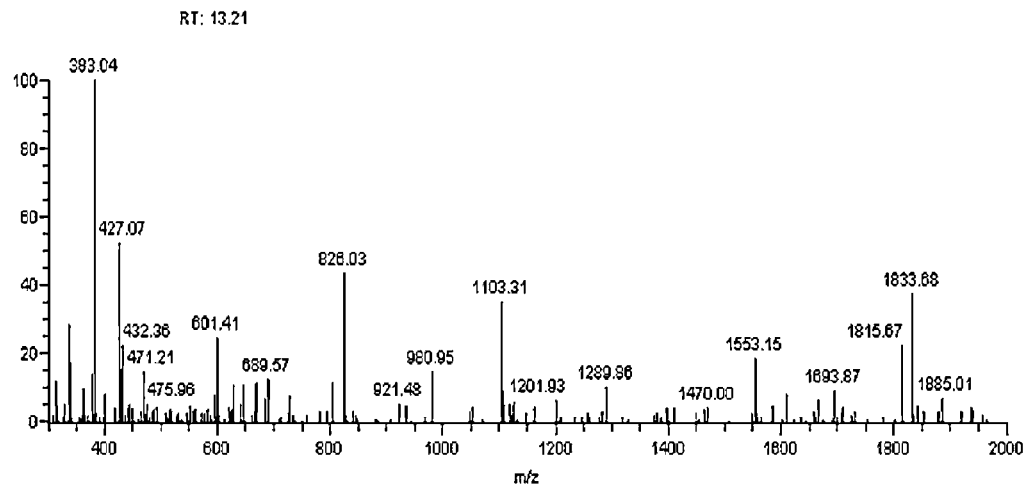
FIGS. 9, 10 shows a mass spectrum of two non enantiomers of MDC-MCC-Lysine, which was the metabolites of D-Lmcc-anti-Her2 antibody.
Figure 10:
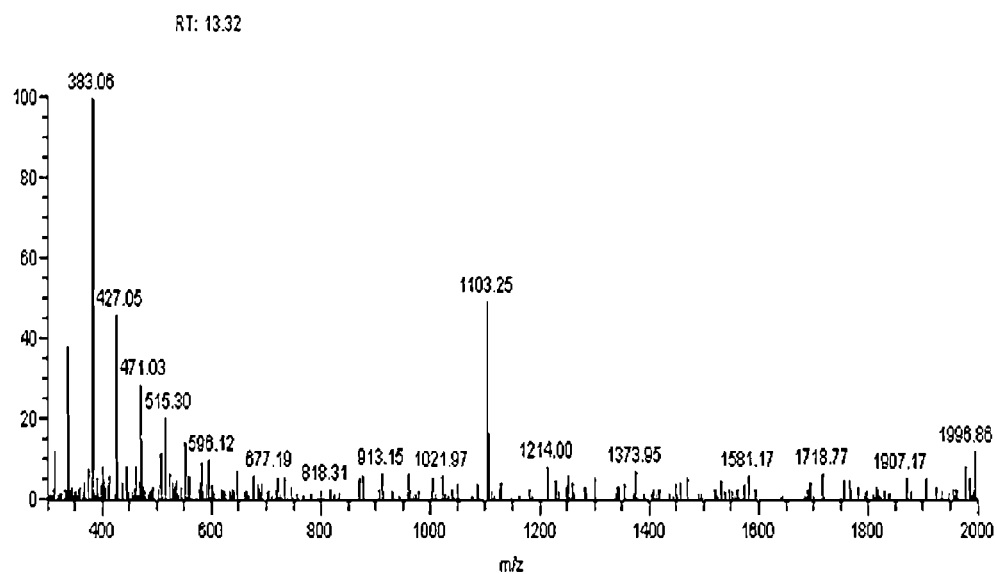

Cellular Metabolites of 3AAMDC-antibody and D-Lmcc-anti-Erb B2 antibody were assayed as described in Erickson, et al. Cancer Res 66:4426-4433 (2006). Briefly, A431 cells ($6 \times 10^6$) suspended in 3 mL culture medium containing 3AAMDC-antibody at a concentration of $10^{-7}$ mol/L of conjugated antibody were incubated at 37° C. for 3 to 30 hours. The cells and the medium were then separated by centrifugation (2,000×g, 5 minutes). The supernatant (3 mL) was chilled on ice, mixed with 4 mL ice-cold acetone, and kept at −80° C. for at least 1 hour or until further processing. Precipitated protein was removed by centrifugation at 2,500×g and the supernatants were acidified with 5% acetic acid and evaporated to dryness. The samples were dissolved in 0.12 mL of 20% aqueous CH3CN containing 0.025% trifluoroacetic acid (TFA), aliquots of 0.1 mL were submitted to LC-MS (FIGS. 8, 9, 10).

What is claimed is:

1. A method of treating HER2 expressing breast cancer or HER2 expressing gastric cancer in a patient in need thereof comprising administering an effective amount of a compound of Formula 1a:

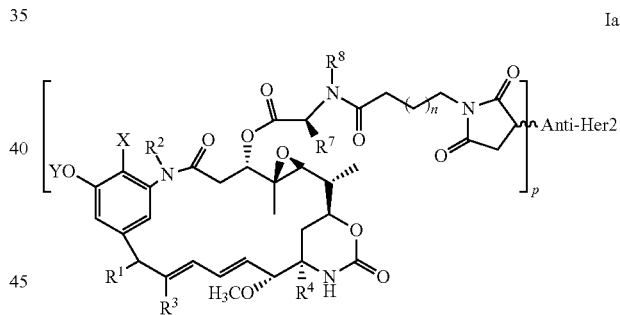

Ia or a salt thereof,
wherein
X is hydrogen or halo;
Y is selected from the group consisting of hydrogen, $C_1$-$C_6$ alkyl, $C_3$-$C_6$ cycloalkyl, and —C(=O)R$^5$;
$R^1$ is selected from the group consisting of hydrogen, —OH, —OC(=O)R$^5$ and —OR$^5$;
$R^2$ is hydrogen or $C_1$-$C_6$ alkyl;
$R^3$ is methyl, —CH$_2$OH, or —CH$_2$C(=O)R$^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
n is 0, 1, 2, 3, 4, 5, 6, 7 or 8;
p is selected from 1, 2, 3, 4, 5, 6, 7, 8, 9, 10; and
Anti-HER2 is an anti-ERB B2/NEU (HER2) antibody.

2. A method of treating HER2 expressing breast cancer or HER2 expressing gastric cancer in a patient in need thereof comprising administering an effective amount of a compound of Formula 1a:

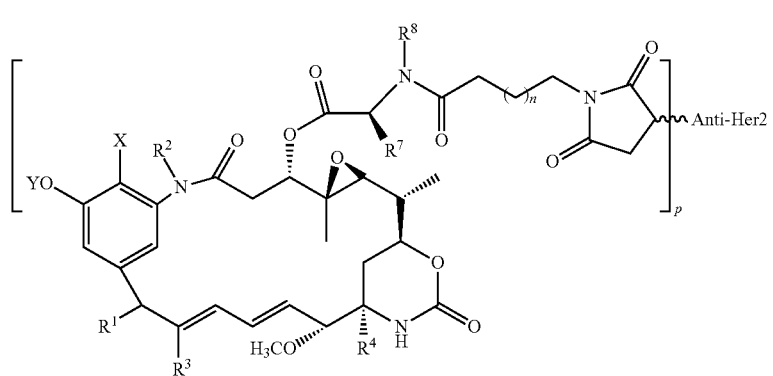
or a salt thereof,
wherein
X is Cl;
Y is $C_1$-$C_6$ alkyl;
$R^1$ is hydrogen;
$R^2$ is $C_1$-$C_6$ alkyl;
$R^3$ is methyl;
$R^4$ is —OH;
$R^7$ is $C_1$-$C_6$ alkyl; and
$R^8$ is $C_{1-6}$ alkyl;
n is 0, 1, 2, 3, 4, 5, 6, 7 or 8;
p is selected from 1, 2, 3, 4, 5, 6, 7, 8, 9, 10; and
Anti-HER2 is an anti-ERB B2/NEU (HER2) antibody.
* * * * *